US008742204B2

(12) United States Patent
Turano et al.

(10) Patent No.: US 8,742,204 B2
(45) Date of Patent: Jun. 3, 2014

(54) METABOLIC REGULATORS

(75) Inventors: Frank J. Turano, Baltimore, MD (US); Kathleen A. Turano, Baltimore, MD (US)

(73) Assignee: Plant Sensory Systems, LLC, Baltimore, MD (US)

( * ) Notice: Subject to any disclaimer, the term of this patent is extended or adjusted under 35 U.S.C. 154(b) by 251 days.

(21) Appl. No.: 13/095,261

(22) Filed: Apr. 27, 2011

(65) Prior Publication Data

US 2011/0231961 A1 Sep. 22, 2011

Related U.S. Application Data

(63) Continuation-in-part of application No. 12/200,060, filed on Aug. 28, 2008, now abandoned.

(60) Provisional application No. 60/968,730, filed on Aug. 29, 2007.

(51) Int. Cl.

| | |
|---|---|
| ***A01H 5/00*** | (2006.01) |
| ***C07K 14/195*** | (2006.01) |
| ***C12N 15/82*** | (2006.01) |
| ***C12N 15/62*** | (2006.01) |

(52) U.S. Cl.

USPC ........ 800/290; 800/288; 800/295; 800/320.1; 530/350; 536/23.4; 435/69.7; 435/69.8; 435/468; 435/419

(58) Field of Classification Search

None

See application file for complete search history.

(56) References Cited

U.S. PATENT DOCUMENTS

| | | | | |
|---|---|---|---|---|
| 7,432,353 | B2 | 10/2008 | Lee et al. | |
| 2005/0112685 | A1 * | 5/2005 | Amiss et al. | 435/7.1 |
| 2006/0078908 | A1 | 4/2006 | Pitner | |
| 2007/0136825 | A1 * | 6/2007 | Frommer et al. | 800/3 |

FOREIGN PATENT DOCUMENTS

| | | | |
|---|---|---|---|
| WO | 03025220 | A2 | 3/2003 |
| WO | 2005038006 | A2 | 4/2005 |

OTHER PUBLICATIONS

Tam, R. and M.H. Saier, Jr., "Structural, functional, and evolutionary relationships among extracellular solute-binding receptors of bacteria," Microbiological Reviews 57(2):320-346, 1993.

Tame, J. et al., "The crystal structures of the oligopeptide-binding protein OppA complexed with tripeptide and tetrapeptide ligands," Structure 3(12):1395-1406, 1995.

Wroblewska, B. et al., "N-Acetylaspartylglutamate selectively activates mGluR3 receptors in transfected cells," J. of Neurochemistry 69(1):174-181, 1997.

Supplemental Search Report dated Oct. 13, 2010, in related application No. EP 08 79 8870, 5 pages.

* cited by examiner

*Primary Examiner* — Medina A Ibrahim
*Assistant Examiner* — Lee A Visone
(74) *Attorney, Agent, or Firm* — Rothwell, Figg, Ernst & Manbeck P.C.

(57) ABSTRACT

The present invention provides metabolic regulators, which are proteins (such as fusion proteins, truncated proteins or full-length proteins) that bind to specific metabolites and which can be used to control the availability of the metabolites in cells, particularly plant cells. Proteins of the invention include one or more metabolic regulator proteins, can be truncated or full length, can further comprise a transmembrane domain or lipoylation site or can further comprise a transit peptide. Metabolic regulators of the invention can be soluble, e.g., cytosolic soluble, can be anchored to a biological membrane or can be organelle targeted or apoplastic targeted. The present invention also provides nucleic acid molecules encoding the metabolic regulators, methods of making the nucleic acid molecules, methods for making transformed organisms, including plants, photosynthetic organisms, microbes, invertebrates, and vertebrates, and methods for controlling availability of metabolites to a host cell.

15 Claims, 3 Drawing Sheets

METABOLIC REGULATORS

CROSS-REFERENCE TO RELATED APPLICATIONS

The present application is a continuation-in-part application of U.S. patent application Ser. No. 12/200,060 filed 28 Aug. 2008 which in turn is related to and claims priority under 35 U.S.C. §119(e) to U.S. provisional patent application Ser. No. 60/968,730 filed on 29 Aug. 2007. Each application is incorporated herein by reference.

SEQUENCE SUBMISSION

The present application is being filed along with a Sequence Listing in electronic format. The Sequence Listing is entitled 3834109SequenceListing.txt, was created on 5 Apr. 2011 and is 20 kb in size. The information in the electronic format of the Sequence Listing is part of the present application and is incorporated herein by reference in its entirety.

FIELD OF THE INVENTION

The invention relates to metabolic regulation.

BACKGROUND OF THE INVENTION

The present invention provides metabolic regulators, which are proteins (such as fusion proteins, truncated proteins or full-length proteins) that bind to specific metabolites and which can be used to control the availability of the metabolites in cells, particularly plant cells. The proteins of the invention include one or more metabolic regulator proteins, such as bacterial periplasmic binding proteins (bPBPs) or domains from prokaryotic and eukaryotic proteins that are functionally similar to the bPBPs. The present invention also provides nucleic acid molecules encoding the metabolic regulators, methods of making the nucleic acid molecules, and methods for making transformed organisms, including plants, photosynthetic organisms, microbes, invertebrates, and vertebrates.

The publications and other materials used herein to illuminate the background of the invention, and in particular, cases to provide additional details respecting the practice, are incorporated by reference in their entirety for all that they disclose, and for convenience are referenced in the following text by reference number and are listed by reference number in the appended bibliography.

Plants need resources in the form of elements such as carbon, nitrogen, sulfur, phosphate, hydrogen, oxygen and minerals, for normal growth and development. The resources can be absorbed from the air and soil in the form of carbon dioxide, ammonium, nitrate, phosphates, water, oxygen and ions. Some resources must be assimilated and are synthesized into more complex molecules such as sugars, lipids, amino acids, nucleotides and a variety of secondary molecules that are necessary for plant growth, development, and reproduction. Many of the molecules, such as carbon and nitrogen, form the building blocks for biological polymers, such as polypeptides, DNA, RNA, starch, and cellulose, which regulate and sustain life. Furthermore, water up-take and usage is also associated with the utilization of the above-mentioned compounds.

Plants must coordinate the up-take, assimilation, distribution, allocation and mobilization of resources in the form of carbon, nitrogen, sulfur, phosphate and ions to maximize growth and development, and to maintain health and their ability of reproduce through fruit and seed production. To coordinate these processes plants have developed complex monitoring and signaling networks that integrate the up-take, synthesis, distribution, and allocation of resources available to the plant (31, 32, 33, 38, 58, 89, 94, 95, 152, 154, 165, 166, 171). Recent findings indicate that plants monitor these processes through a set of receptors called plant glutamate receptors that bind to metabolites, specifically amino acids (31, 38, 49, 60, 99, 154).

There is a need in the art for compositions and methods of controlling the availability of metabolites in cells, particularly plant cells.

SUMMARY OF THE INVENTION

The present invention provides metabolic regulators, which are proteins (such as fusion proteins, truncated proteins or full-length proteins) that bind to specific metabolites (such as known in the art) and which can be used to control the availability of the metabolites in cells, particularly plant cells. Proteins of the invention include one or more metabolic regulator proteins, such as bacterial periplasmic binding proteins (bPBPs) or domains from prokaryotic and eukaryotic proteins that are functionally similar to the bPBPs. The metabolic regulator proteins may be truncated or may be full length. Metabolic regulators of the invention can be soluble, e.g., cytosolic soluble, or can further comprise a transmembrane domain or lipoylation site, which permits the protein to be anchored to a biological membrane. Additionally, the proteins of the invention can also comprise a transit peptide. Such metabolic regulators of the present invention can be organelle targeted or apoplastic targeted. Changes in metabolite availability will result in altered metabolism or receptor activity to improve growth, yield, crop quality (such as increased, seed weight, oil content, seed oil content, lignin, sugar content or cellulose), or tolerance to biotic and abiotic stress.

The invention also provides nucleic acid molecules encoding the metabolic regulators, methods of making the nucleic acid molecules, and methods for making transformed organisms, including plants, photosynthetic organisms, microbes, invertebrates, and vertebrates. The invention also provides methods of controlling availability of metabolites to a host cell.

BRIEF DESCRIPTION OF THE FIGURES

FIG. 1A shows the proposed structure of a bPBP (black, half circles). FIG. 1B shows the proposed structure of a bacterial glutamate receptor that contains a LAOBP-LD in the middle of the molecule (hatched half circles), two transmembrane domains and a pore-forming domain (labeled "1," "2," and "P," respectively, in FIG. 1B). FIG. 1C shows the proposed structure of an animal AMPA, KA or delta ionotropic glutamate receptor, and some rice glutamate receptors that contain a LAOBP-LD in the middle of the molecule (hatched, half circles), three transmembrane domains and a pore-forming domain (labeled "1," "2," "3," and "P," respectively, in FIG. 1C). FIG. 1D shows the proposed structure of an animal NMDA ionotropic glutamate receptor, *Arabidopsis thaliana* glutamate receptor, and most rice glutamate receptors that contain a LIVBP-LD in the amino terminus (white, half circles) and LAOBP-LD in the middle of the molecule (hatched, half circles), three transmembrane domains and a pore-forming domain (labeled "1," "2," and "3" and "P," respectively, in FIG. 1D). FIG. 1E shows the proposed structure of a member of the family C of the G-protein coupled receptors that contain a LIVBP-LD in the amino terminus (white, half circles) and the seven transmembrane domains (labeled "1" through "7" in FIG. 1E). Family C of G-protein coupled receptors includes metabotropic glutamate receptors, gamma-aminobutyric acid-B receptors, calcium sensor receptors, pheromone receptors, taste receptors, odorant receptors, sweet receptors, amino acid amino acid receptors or orphan receptors. FIG. 1F shows the proposed structure of an atrial natriuretic peptide receptor that contains a LIVBP-LD (the extracellular ligand binding domain) in the amino terminus (white, half circles), a single transmembrane domain (labeled "1" in FIG. 1F), a protein kinase-like domain (gray, oval), a dimerization domain (white, diamond) and a carboxyl-terminal guanylyl cyclase domain (dotted, octagon). In each diagram the two horizontal lines represent a membrane, and the inside and outside locations of the cell are indicated.

FIG. 2A is a single anchored metabolic regulator. The transmembrane domain is labeled "1" in FIG. 2A. FIG. 2B is a multiple fused anchored metabolic regulator. The transmembrane domain is labeled "1" in FIG. 2B. FIG. 2C is a multiple fused anchored metabolic regulator with either a bPBP or a eukaryotic protein that contains domains that are functionally similar to the bPBPs on either side of the membrane. The transmembrane domain is labeled "1" in FIG. 2C. FIG. 2D is a multiple fused anchored metabolic regulator with either a bPBP or a eukaryotic protein that contains domains that are functionally similar to the bPBPs on one side of the membrane and two or more (*) bPBPs or a eukaryotic protein that contains domains that are functionally similar to the bPBPs on the other side of the membrane. The transmembrane domain is labeled "1" in FIG. 2D. FIG. 2E is a multiple fused anchored metabolic regulator with at least two bPBPs or two eukaryotic proteins that contain domains that are functionally similar to the bPBPs on either side of the membrane. The transmembrane domain is labeled "1" in FIG. 2E. FIG. 2F is a single soluble metabolic regulator. FIG. 2G is a multiple fused soluble metabolic regulator. In each diagram the two vertical lines represent a membrane, and the gray half circles represent a bPBP or a eukaryotic protein that contains a domain that is functionally similar to the bPBPs, either a LIVBP-LD or a LAOBP-LD. The locations of the polypeptides within the cell or cellular compartment are not indicated because, as described below, the polypeptides can be on the outside or inside of the cell or cellular compartment.

DETAILED DESCRIPTION OF THE INVENTION

Figure 1:
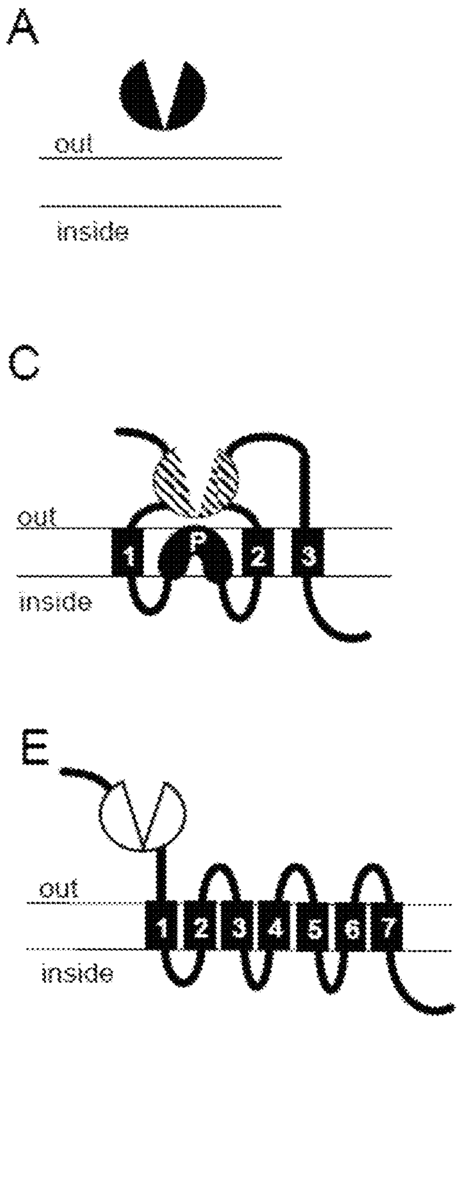
FIGS. 1A-1F show schematic representations of structures of bPBPs and eukaryotic proteins that contain domains that are functionally similar to the bPBPs, called the LIVBP-LD and LAOBP-LD. A comparison among the representations reveals the structural similarities.
Figure 2:
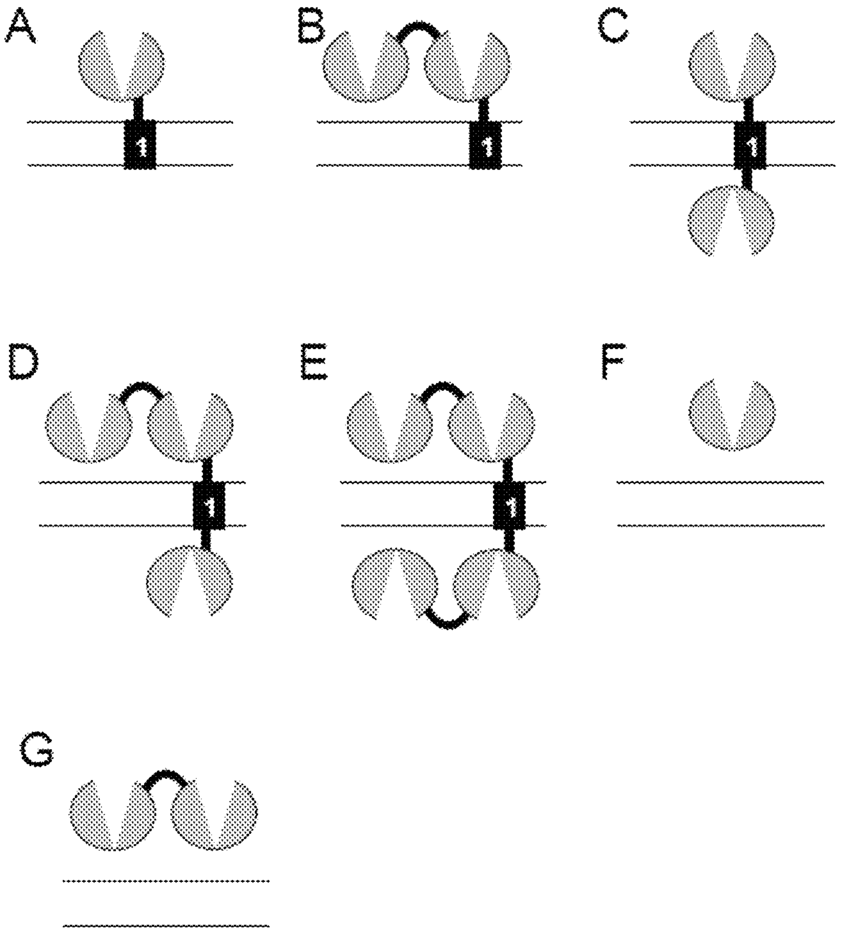
FIGS. 2A-2G show proposed protein structure of the functional anchored and soluble metabolic regulators.

The present invention provides metabolic regulators, which are proteins (such as fusion proteins, truncated proteins or full-length proteins) that bind to specific metabolites (such as known in the art) and which can be used to control the availability of the metabolites in cells, particularly plant cells. Proteins of the invention include one or more metabolic regulator proteins, such as bacterial periplasmic binding proteins (bPBPs) or domains from prokaryotic and eukaryotic proteins that are functionally similar to the bPBPs. The metabolic regulator proteins may be truncated or may be full length. Metabolic regulators of the invention can be soluble, e.g., cytosolic soluble, or can further comprise a transmembrane domain or lipoylation site, which permits the protein to be anchored to a biological membrane. Additionally, the proteins of the invention can also comprise a transit peptide. Such metabolic regulators of the present invention can be organelle targeted or apoplastic targeted. Changes in metabolite availability will result in altered metabolism or receptor activity to improve growth, yield, crop quality, or tolerance to biotic and abiotic stress.

The invention also provides nucleic acid molecules encoding the metabolic regulators, methods of making the nucleic acid molecules, and methods for making transformed organisms, including plants, photosynthetic organisms, microbes, invertebrates, and vertebrates. The invention also provides methods of controlling availability of metabolites to a host cell. In one method, a host cell comprising a protein, such as those described herein, including a full length metabolic regulator, is contacted with an amino acid.

Thus, in one embodiment, a protein of the present invention comprises a truncated metabolic regulator. In another embodiment, a protein of the present invention comprises a full length metabolic regulator. In an additional embodiment, a protein of the present invention is a first fusion protein which comprises (i) a first polypeptide segment and (ii) a second polypeptide segment. The first polypeptide segment comprises a first metabolic regulator protein. The second polypeptide segment comprises either (1) a transmembrane domain or a lipoylation recognition site, whereby the fusion protein can be anchored to a biological membrane, or (2) a second metabolic regulator protein. In the first fusion protein, the N terminus of the second polypeptide segment is linked to the C terminus of the first polypeptide segment when the second polypeptide segment is a transmembrane domain or a lipolyation recognition site. In the first fusion protein, the C terminus of the first polypeptide segment is linked to the N terminus of the second polypeptide segment when the second polypeptide segment is a transmembrane domain. In the first fusion protein, the first polypeptide segment and the second polypeptide segment can be fused in either order when the first and second polypeptide segments are a first and a second metabolic regulator proteins. In a further embodiment, a protein of the present invention comprises a second fusion protein comprising (i) a transit peptide and (ii) another peptide. The other peptide comprises either (1) a truncated first metabolic regulator, (2) a full length first metabolic regulator or (3) the first fusion protein. In the second fusion protein, the transit peptide is the N terminus of the second fusion protein

Metabolic Regulator Proteins

Metabolic regulator proteins useful as truncated proteins or as fusion proteins of the invention include bacterial periplasmic binding proteins and proteins which contain a domain functionally similar to a bacterial periplasmic binding protein.

Bacterial Periplasmic Binding Proteins

BPBPs are soluble proteins in the periplasmic space that bind and transport nutrients (55). The bPBPs can be divided into different classes, families, or groups that can range from 1 to 8 different groups, depending on the nomenclature used. The sequence similarity among the members of the same group is well conserved but the primary sequences among members of different families can be very diverse. Yet, the tertiary structure, or three-dimensional configuration, among all the members of the bPBPs is well conserved. The tertiary structure forms a lobe-hinge-lobe region with two lobes that look like a bivalve, or clam (FIG. 1A). Upon exposure of the target molecule, or ligand, the bivalves close similar to a Venus flytrap for which the molecular model is named.

Proteins that Contain a Domain Functionally Similar to the Bacterial Periplasmic Binding Proteins The Venus-flytrap mechanism is also conserved among specific regions of the bacterial glutamate receptors and in some eukaryotic proteins (55, 66, 90, 96, 123, 124, 144, 150, 157, 195). The regions corresponding to the Venus-flytrap mechanism reside in specific domains called the leucine-isoleucine-valine-binding protein-like domain (LIVBP-LD) or the lysine-arginine-ornithine-binding protein-like domain (LAOBP-LD) of the bacterial glutamate receptors and in the eukaryotic ionotropic glutamate receptors (55), plant glutamate receptors (24, 25, 183), members of the family C of G-protein coupled receptors (55, 102, 140), and atrial natriuretic peptide receptors (55, 153). Although the functions of the proteins are diverse, ranging from nutrient binding and transport in bacteria to neuronal signaling in humans, the function of the Venus-flytrap mechanism is similar in that it binds specific molecules called ligands.

Bacterial Glutamate Receptors

To date only one bacterial glutamate receptor has been identified, and it is in the photosynthetic bacteria, *Synechosystis* PCC 6803 (20). The receptor is located on the outer membrane and uses a Venus-flytrap mechanism, which resides in a domain that is functionally similar to the bPBPs called the LAOBP-LD (FIG. 1B). The LAOBP-LD, located in the middle of the molecule, is interrupted by a pore-forming domain and flanked by two transmembrane domains (labeled as "1" and "2" in FIG. 1B). Unlike the animal ionotropic glutamate receptors, the bacterial glutamate receptor does not have the amino terminal domain, the last transmembrane domain, or the cytoplasmic carboxyl-tail. The bacterial glutamate receptors have broad ligand selectivity that controls potassium influx.

Eukaryotic Ionotropic Glutamate Receptors

The ionotropic glutamate receptors are classified into four distinct pharmacological subtypes based on agonist selectivity and ion-conductance (7): N-methyl-D-aspartate (NMDA), alpha-amino-3-hydroxy-5-methyl-isoxazole-4-propionic acid (AMPA), kainic acid (KA) and delta receptors (43, 191). The NMDA receptors contain a domain that is functionally similar to the bPBPs in the amino terminus called the LIVBP-LD. The receptors bind modulators, such as zinc, polyamines, and ifenprodil (92, 300). There is another domain that is functionally similar to the bPBPs in the middle of the molecule, called the LAOBP-LD, which binds the ligand or agonist(s), to activate the receptor (125, 126). The receptor contains three transmembrane domains (labeled as "1," "2," and "3" in FIG. 1D) and one pore-forming domain. The AMPA, KA and delta receptors (FIG. 1C) are structurally similar to the NMDA receptors but they lack the LVIBP-LD in the amino terminal region. In animals the ionotropic glutamate receptors are located on the plasma membrane and control signaling across the synapse, i.e., a small gap between adjacent neurons (121). They are activated upon the binding of a specific ligand that causes a conformational change in the LAOBP-LD. This, in turn, opens the pore to allow cations, typically sodium, potassium or calcium, to enter the cell (125).

Plant Glutamate Receptors

Plants, such as *Arabidopsis* (115) and rice (69, 199), also contain ionotropic glutamate receptors homologs. There are twenty ionotropic glutamate receptors homologs in the plant *Arabidopsis*, designated as the *Arabidopsis thaliana* glutamate receptors, and 23 glutamate receptors in rice, designated as the rice glutamate receptors. All *Arabidopsis thaliana* glutamate receptors and most rice glutamate receptors are structurally similar to the animal NMDA ionotropic glutamate receptors (FIG. 1D) (43, 60), i.e. they have the amino terminal LIVBP-LD (183), the LAOBP-LD, three transmembrane domains, and one pore-forming domain (24, 25, 115). Other rice glutamate receptors are structurally similar to the animal AMPA, KA, and delta receptors in that they lack the LIVBP-LD in the amino terminal region (FIG. 1C). Several plant glutamate receptors have been localized on the plasma membrane (97, 130). To date, the ligands for the plant receptors have not been definitively identified, however several amino acids have been associated with changes in the electrophysiological and physiological measures and to intercellular calcium increases (45, 48, 154). The plant glutamate receptors are involved in the regulation of carbon (49, 99) and nitrogen metabolism (99), hormone (abscissic acid) biosynthesis and signaling (98, 99), calcium homeostasis (105), and biotic (97) and abiotic stress response (130).

Family C of G-Protein Coupled Receptors

In animals there is another family of functionally diverse receptors that have a domain that is functionally similar to the bPBPs in the amino terminus Members of family C (109), also called family III (145) or family G (100), of the G-protein coupled receptors are grouped together because they have a large (350 to 700 amino acid) extracellular domain. Similar to all G-coupled receptor proteins, the proteins have seven transmembrane domains (FIG. 1E). Located in the amino terminus of the receptor is a domain that is functionally similar to the bPBPs called the LIVBP-LD. Family C of the G-protein coupled receptors includes a host of receptors such as the metabotropic glutamate receptors, gamma-aminobutyric acid-B receptors, calcium sensor receptors, pheromone receptors, taste receptors, odorant receptors, sweet receptors, amino acid amino acid receptors or orphan receptors. Members of family C of the G-protein coupled receptors are located on the plasma membrane of various organs, including the nervous system, kidney parathyroid cells and vomeronasal organ. Members of family C of the G-protein coupled receptors are activated upon the binding of a specific ligand that results in a conformational change in the LIVBP-LD. This in turn changes the conformation of the seven transmembrane domain region, which activates down stream signaling events through a trimeric G-protein.

Atrial Natriuretic Peptide Receptors

The atrial natriuretic peptide receptors are composed of an extracellular domain that is functionally similar to the bPBPs, a single transmembrane domain, a protein kinase-like domain, a dimerization domain, and a carboxyl-terminal guanylyl cyclase domain (FIG. 1F). The extracellular domain is homologous to the LIVBP-LD of the metabotropic glutamate receptors. The atrial natriuretic peptide receptors are located on the plasma membrane in various tissues and function in the regulation and control of blood pressure and body fluid homeostasis (55). The ligand for the LIVBP-LD of the atrial natriuretic peptide receptors is the atrial natriuretic peptide, which is an oligopeptide (153).

Thus, metabolic regulator proteins useful in the invention include, but are not limited to, bPBPs, periplasmic binding protein-like I, periplasmic binding protein-like II, or proteins in the superfamily of extracellular or periplasmic solute-binding proteins, families 1 through 8, or any of the following periplasmic binding proteins including, but not limited to, periplasmic arabinose binding proteins (ABP), periplasmic ribose-binding proteins (RBP), periplasmic allose-binding proteins, periplasmic glucose-galactose-binding proteins (GGBP), quorum-sensing binding proteins, periplasmic leucine-isoleucine-valine-binding proteins, periplasmic leucine-binding proteins, periplasmic phosphate binding protein (PhosBP), periplasmic maltose-maltodextrin-binding proteins, periplasmic multiple oligo-saccharide binding proteins, periplasmic glycerol-3-phosphate-binding proteins, periplasmic iron-binding proteins (FeBP), periplasmic thiamine-binding proteins (tbpA), periplasmic histidine-binding proteins (HBP), periplasmic lysine-arginine-ornithine-binding proteins, periplasmic glutamine-binding proteins (QBP), periplasmic glutamate-binding proteins (GluBP), periplasmic arginine-binding proteins, major cell-binding factor (CBF1), protein aabA, cyclohexadienyl/arogenate dehydratase, periplasmic oligopeptide-binding proteins (OppA), periplasmic dipeptide-binding proteins (DPBP), periplasmic murein peptide-binding protein, periplasmic peptide-binding proteins, periplasmic nickel-binding protein, heme-binding lipoprotein, lipoprotein xP55, protein HI0213, protein y4tO, and protein y4wM, periplasmic glucose-galactose-mannose-binding protein, periplasmic trehalose-maltose-binding protein, periplasmic maltose binding protein (MBP), periplasmic multiple oligo-saccharide binding, periplasmic arabinose-fructose-xylose-binding protein, periplasmic iron dictate-binding protein, periplasmic taurine-binding protein, periplasmic phosphonate-binding protein, periplasmic zinc-binding protein, periplasmic C4-dicarboxylate-binding protein, periplasmic dicarboxylate-binding protein, periplasmic succinate-malate-fumarate binding protein, sorbitol-binding protein, periplasmic molybdate-binding protein, periplasmic putrescine-spermidine-binding protein, periplasmic polyamine-binding protein, periplasmic betaine-binding protein, periplasmic proline-glycine-betaine-binding protein, periplasmic glutamate-aspartate binding protein, periplasmic thiamin-(vitamin B1) binding protein, periplasmic vitamin B12-binding protein, periplasmic thiosulfate-binding protein, enterobactin-Fe binding protein, ferrichydroxamate-binding protein, periplasmic cystine-binding protein, periplasmic gluconate-binding protein, and periplasmic L-alanyl-gamma-D-glutamyl-binding protein.

Other metabolic regulator proteins useful in the invention include domains from prokaryotic and eukaryotic proteins that are functionally similar to the bPBPs. These include, but are not limited to, proteins from the following families of bacterial and eukaryotic proteins that contain a LIVBP-LD or a LAOBP-LD.

LAOBP-LD refers to regions of a protein that contain a peptide sequence that (i) is related to the periplasmic binding proteins, either class I and II, (ii) can selectively hybridize to the nucleotide sequence corresponding to the amino acid sequences that flank (approximately 130 to 160 residues to either side), the pore-forming domains in the bacterial glutamate receptor, plant glutamate receptor, glutamate receptor from a photosynthetic organism or autotrophic organism, or vertebrate or invertebrate ionotropic glutamate receptors, (iii) has substantial identity with the amino acid sequences that flank (approximately 130 to 160 residues to either side), the pore-forming domains in the bacterial glutamate receptor, plant glutamate receptor, glutamate receptor from a photosynthetic organism or autotrophic organism, or vertebrate or invertebrate ionotropic glutamate receptors, or (iv) has the ability to form a Venus-flytrap mechanism.

LIVBP-LD refers to regions of a protein that contain a peptide sequence that (i) is related to the periplasmic binding proteins, either class I and II, (ii) contains the LIVBP consensus sequence [S]-x(22)-[TS]-x(13,14)-[R]-x(4)-[D]-x(2)-[Q]-x(24,25)-[Y]-[GA]-x(74,84)-[D] (1) (iii) can selectively hybridize to the nucleotide sequence corresponding to the amino acid sequence from amino acid residue 10 to 550 from any of the following gene or protein families; plant glutamate receptor, NMDA receptors from animals, a member of family C of the G-protein coupled receptors or atrial natriuretic peptide receptors (iv) has substantial identity of amino acid sequences in the amino terminus (approximately the amino acid residues 1 to 550) with NMDA receptors from animals, *Arabidopsis* glutamate receptors 1.1, 1.2, 1.3, 1.4, 2.1, 2.2, 2.3, 2.4, 2.5, 2.6, 2.7, 2.8, 2.9, 3.1, 3.2, 3.3, 3.4, 3.5, 3.6, and 3.7, any of the 23 rice glutamate receptors, members of family C of the G-protein coupled receptors or atrial natriuretic peptide receptors. Members of family C of the G-protein coupled receptors include but are not limited to metabotropic glutamate receptors (mGLRs), gamma-aminobutyric acid B receptors ($GABA_B$-R), calcium sensor receptors, pheromone receptors, taste receptors, odorant receptors, sweet receptors, amino acid amino acid receptors or orphan receptors, or (v) has the ability to form a Venus-flytrap mechanism.

Persons of ordinary skill in the art can identify a LIVBP-LD, a LAOBP-LD, or domains that are similar to bPBPs, in that they have a tertiary structure that forms a lobe-hinge-lobe region, or two lobes, that bind to a ligand, agonist or antagonist by a Venus-flytrap mechanism.

Other suitable proteins that contain a domain that is functionally similar to the bPBPs can be obtained from a bacterial glutamate receptor, plant glutamate receptor, glutamate receptor from a photosynthetic organism or autotrophic organisms, vertebrate or invertebrate ionotropic glutamate receptor, members of the family C of the G-protein-coupled receptors from vertebrates or invertebrates and atrial natriuretic peptide receptors.

Transmembrane Domains

Transmembrane domains useful in the present invention include, but are not limited to, those from the following families of proteins: bacterial glutamate receptors, plant glutamate receptors (including, but not limited to, *Arabidopsis thaliana* and rice), vertebrate and invertebrate ionotropic glutamate receptors, vertebrate and invertebrate atrial natriuretic peptide receptors and any member of the G-protein coupled receptors. In the preferred forms of the invention, the transmembrane domain should form an alpha helix, however a transmembrane domain formed from a beta sheet may be suitable. Persons of ordinary skill in the art can identify nucleotides that encode polypeptides for transmembrane domains using computer programs that predict the formation of a hydrophobic alpha helix of 20 to 25 amino acid residues. Hydrophobicity-hydrophilicity profiles of a polypeptide can be obtained for proteins by the Kyte-Doolittle method (13).

Numerous transmembrane prediction programs are available, including, but not limited to, DAS (41), TopPred 2 (188), Tmpred (85), PRED-TMR (146), HMMTOP (184, 185), SOSUI: (84), TMH Benchmark (22, 104), and DAS-TMfilter (40), BPROMPT (http colon//www dot jenner dot ac dot uk/BPROMPT/). Two resources that have lists of transmembrane-containing proteins with the transmembrane domain delineated are THGS (57) and ARAMEMNON (161). In addition, transmembrane domains can be identified using computer programs that can predict the formation of hydrophobic beta strands including, but not limited to, TBBpred (136) and TMBETA-NET (73).

Lipoylation Sites

Persons of ordinary skill in the art can also target proteins to membranes using lipoylation, which is a posttranslational modification that adds a lipid molecule to a polypeptide. Lipoylation includes, but is not limited to, prenylation (farnesylation), myristoylation, and geranylgeranylation (50). For example, the addition of the polypeptide CAAX at the carboxy-terminus of a functional bPBP or to a domain from a prokaryotic or eukaryotic protein that is functionally similar to the bPBPs would target or anchor the polypeptide to a membrane.

Nucleic Acid Molecules

The present invention provides nucleic acid molecules (polynucleotides) that encode metabolic regulators of the invention. Nucleic acid molecules that encode components of the metabolic regulators described above are known in the art. Other polynucleotides for use in the invention may be obtained by the identification of polynucleotides that selectively hybridize to the polynucleotides encoding the metabolic regulator proteins described above by hybridization under low stringency conditions, moderate stringency conditions, or high stringency conditions. Still other suitable polynucleotides for use in accordance with the invention may be obtained by the identification of polynucleotides that encode polypeptides that have substantial identity of the nucleic acid or amino acid sequence using the nucleic acid or amino acid sequence of the bPBPs listed above as a reference for sequence comparison.

Other suitable polynucleotides for use in accordance with the invention may be obtained by the identification of polynucleotides that selectively hybridize to the polynucleotides of the LIVBP-LD or LAOBP-LD of the proteins listed above by hybridization under low stringency conditions, moderate stringency conditions, or high stringency conditions. In addition, other suitable polynucleotides for use in accordance with the invention may be obtained by the identification of polynucleotides that encode polypeptides that have substantial identity to the nucleic acid or amino acid sequences of the LIVBP-LD or LAOBP-LDs listed above using the nucleic acid or amino acid sequence as a reference for sequence comparison.

Protein and Nucleic Acid Variants Useful in the Invention

Those of ordinary skill in the art know that organisms of a wide variety of species commonly express and utilize homologous proteins, which include the insertions, substitutions and/or deletions discussed above, and effectively provide similar function. For example, an amino acid sequence isolated from a pBPB or bacterial and eukaryotic proteins that contain a LIVBP-LD or a LAOBP-LD from another species may differ to a certain degree and yet have similar functionality with respect to catalytic and regulatory function. Amino acid sequences comprising such variations are included within the scope of the present invention and are considered substantially or sufficiently similar to a reference amino acid sequence. Although it is not intended that the present invention be limited by any theory by which it achieves its advantageous result, it is believed that the identity between amino acid sequences that is necessary to maintain proper functionality is related to maintenance of the tertiary structure of the polypeptide such that specific interactive sequences will be properly located and will have the desired activity, and it is contemplated that a polypeptide including these interactive sequences in proper spatial context will have activity.

Another manner in which similarity may exist between two amino acid sequences is where there is conserved substitution between a given amino acid of one group, such as a non-polar amino acid, an uncharged polar amino acid, a charged polar acidic amino acid, or a charged polar basic amino acid, with an amino acid from the same amino acid group. For example, it is known that the uncharged polar amino acid serine may commonly be substituted with the uncharged polar amino acid threonine in a polypeptide without substantially altering the functionality of the polypeptide. Whether a given substitution will affect the functionality of the enzyme may be determined without undue experimentation using synthetic techniques and screening assays known to one with ordinary skill in the art.

In one embodiment of the invention, a polynucleotide selected for use in an inventive DNA construct encodes a protein that functions either as a bPBP, a periplasmic binding protein-like I, a periplasmic binding protein-like II, a protein bacterial or eukaryotic protein that contains a LIVBP-LD or a LAOBP-LD. In another embodiment of the invention, a polynucleotide selectively hybridizes polynucleotides that encode a bPBP, a periplasmic binding protein-like I, a periplasmic binding protein-like II, a protein bacterial or eukaryotic protein that contains a LIVBP-LD or LAOBP-LD. Selectively hybridizing sequences typically have at least 40% sequence identity, preferably 60-90% sequence identity, and most preferably 100% sequence identity with each other.

In yet another embodiment of the invention, there is a polynucleotide that encodes a polypeptide that has substantial identity to the amino acid sequence of the bPBP, periplasmic binding protein-like I, periplasmic binding protein-like II, protein bacterial or eukaryotic protein that contains a LIVBP-LD or a LAOBP-LD. Substantial identity of amino acid sequences for these purposes normally means sequence identity of between 50-100%, preferably at least 55%, preferably at least 60%, more preferably at least 70%, 80%, 90%, and most preferably at least 95%.

The process of encoding a specific amino acid sequence may involve DNA sequences having one or more base changes (i.e., insertions, deletions, substitutions) that do not cause a change in the encoded amino acid, or which involve base changes which may alter one or more amino acids, but do not eliminate the functional properties of the polypeptide encoded by the DNA sequence.

It is therefore understood that the invention encompasses more than the specific exemplary polynucleotides encoding the proteins described herein. For example, modifications to a sequence, such as deletions, insertions, or substitutions in the sequence, which produce "silent" changes that do not substantially affect the functional properties of the resulting polypeptide molecule are expressly contemplated by the present invention. Furthermore, because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also describes every possible silent variation of the nucleic acid. One of ordinary skill in the art will recognize that each amino acid has more than one codon, except for methionine and tryptophan that ordinarily have the codons, AUG and UGG, respectively. It is known by those of ordinary skill in the art, "universal" code is not completely universal. Some mitochondrial and bacterial genomes diverge from the universal code, e.g., some termination codons in the universal code specify amino acids in the mitochondria or bacterial codes. Thus each silent variation of a nucleic acid, which encodes a polypeptide of the present invention, is implicit in each described polypeptide sequence and incorporated in the descriptions of the invention.

One of ordinary skill in the art will recognize that changes in the amino acid sequences, such as individual substitutions, deletions or additions to a nucleic acid, peptide, polypeptide, or protein sequence which alters, adds or deletes a single amino acid or a small percentage of amino acids in the encoded sequence is "sufficiently similar" when the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7 or 10 alterations can be made. Conservatively modified variants typically provide similar biological activity as the unmodified polypeptide sequence from which they are derived. For example, receptor activity, ion channel activity or ligand/receptor binding is generally at least 30%, 40%, 50%, 60%, 70%, 80% or 90%, preferably 60-90% of the native protein for its native substrate. Tables of conserved substitution provide lists of functionally similar amino acids.

The following three groups each contain amino acids that are conserved substitutions for one another: (1) alanine (A), serine (S), threonine (T); (2) aspartic acid (D), glutamic acid (E); and (3) asparagine (N), glutamine (Q).

For example, it is understood that alterations in a nucleotide sequence, which reflect the degeneracy of the genetic code, or which result in the production of a chemically equivalent amino acid at a given site, are contemplated. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a biologically equivalent product.

Nucleotide changes which result in alteration of the N-terminal and C-terminal portions of the encoded polypeptide molecule would also not generally be expected to alter the activity of the polypeptide. In some cases, it may in fact be desirable to make mutations in the sequence in order to study the effect of alteration on the biological activity of the polypeptide. Each of the proposed modifications is well within the routine skill in the art.

When the nucleic acid is prepared or altered synthetically, one of ordinary skill in the art can take into account the known codon preferences for the intended host where the nucleic acid is to be expressed. For example, although nucleic acid sequences of the present invention may be expressed in both monocotyledonous and dicotyledonous plant species, sequences can be modified to account for the specific codon preferences and GC-content preferences of monocotyledonous plants or dicotyledonous plants, as these preferences have been shown to differ (134).

Methods of Making Metabolic Regulators

Fusion proteins of the invention (i.e., metabolic regulators) can be made using routine recombinant DNA techniques. In the description which follows, the general schemes are described with reference to a bPBP, but it is understood that any metabolic regulator protein could be used in place of the bPBP. In some embodiments, metabolic regulators which are anchored to a membrane, are prepared according to the following general scheme:

1. fuse the polynucleotide that encodes a bPBP to the polynucleotide for a transmembrane domain such that the transmembrane domain is at the carboxy terminus of the polypeptide;

2. operably link a promoter to the 5' end of the polynucleotides for the functional bPBP fused to a transmembrane domain;

3. insert the polynucleotide construct (from steps 1 and 2 above) into a vector; and 4. transform the vector containing the construct into a plant or plant cell.

In other embodiments the following general schemes can be used:

a. Fusing the polynucleotide for a transmembrane domain to the polynucleotide for a bPBP, such that the transmembrane domain is at the amino terminus of the polypeptide; and repeating steps 2 through 4 from above.

b. Fusing together more than one polynucleotide that encodes the same bPBP or different bPBPs; and repeating steps 1 through 4 from above.

c. Fusing together more than one polynucleotide that encodes the same bPBP or different bPBPs and then fusing the polynucleotides to a transmembrane domain, such that the transmembrane domain is at the amino terminus of the polypeptide; and repeating steps 2 through 4 from above.

d. Fusing two or more polynucleotides that encode the same or different bPBPs to the polynucleotide for a transmembrane domain, such that the resulting polypeptide contains a transmembrane domain flanked on both sides by at least one bPBP; and repeating steps 2 through 4 from above.

e. Fusing the polynucleotide that encodes a bPBP to the polynucleotide for a lipoylation site, such that the lipoylation site is at the carboxy terminus of the polypeptide; and repeating steps 2 through 4 from above.

f. Fusing together more than one polynucleotide that encodes the same bPBP or different bPBPs; and fusing the polynucleotides to the polynucleotide for a lipoylation site, such that the lipoylation site is at the carboxy terminus of the polypeptide; and repeating steps 2 through 4 from above.

Other general schemes for a making soluble metabolic regulator, include:

a. Steps 1 through 4 above, but without a transmembrane domain.

b. Fusing together more than one polynucleotide that encodes the same bPBP or different bPBPs; and repeating steps 1 through 4 from above but without a transmembrane domain.

c. Steps 1 through 4 above, with a truncated bPBP and without a transmembrane domain.

Other general schemes for a making a organelle or apoplastic targeted metabolic regulator, include:

a. Fusing a polynucleotide for a transit peptide to a polynucleotide for a truncated bPBP, such that the transit peptide is at the amino terminus of the polypeptide; and repeating steps 2 through 4 from above but without a transmembrane domain.

b. Fusing a polynucleotide for a transit peptide to a polynucleotide for a bPBP, such that the transit peptide is at the amino terminus of the polypeptide; and repeating steps 2 through 4 from above but without a transmembrane domain.

c. Fusing a polypeptide for a transit peptide with two or more polypeptides for the same bPBP or different bPBPs, such that the transit peptide is at the amino terminus of the polypeptide; and repeating steps 2 through 4 from above but without a transmembrane domain.

d. Fusing a polypeptide for a transit peptide with two or more truncated polypeptides for the same bPBP or different bPBPs, such that the transit peptide is at the amino terminus of the polypeptide; and repeating steps 2 through 4 from above but without a transmembrane domain.

e. Fusing a polypeptide for a transit peptide with two or more polypeptides for the same bPBP or different bPBPs in which at least one of the polypeptides is truncated, such that the transit peptide is at the amino terminus of the polypeptide; and repeating steps 2 through 4 from above but without a transmembrane domain.

Another embodiment for either an anchored or soluble metabolic regulator includes the replacement of the polynucleotides for the bPBPs with the polynucleotides that encode a domain from prokaryotic or eukaryotic proteins that are functionally similar to the bPBPs.

Other suitable polynucleotides for use in accordance with the invention may be obtained by the identification of polynucleotides that selectively hybridize to the polynucleotides of the domains that are functionally similar to the bPBPs listed above by hybridization under low stringency conditions, moderate stringency conditions, or high stringency conditions. Still other suitable polynucleotides for use in accordance with the invention may be obtained by the identification of polynucleotides that encode polypeptides that have substantial identity of the nucleic acid or amino acid sequence using the nucleic acid or amino acid sequence for the domains that are functionally similar to the bPBPs listed above as a reference for sequence comparison.

Cloning Techniques

For purposes of promoting an understanding of the principles of the invention, reference will now be made to particular embodiments of the invention and specific language will be used to describe the same. The materials, methods and examples are illustrative only and not limiting. Unless mentioned otherwise, the techniques employed or contemplated herein are standard methodologies well known to one of ordinary skill in the art. Specific terms, while employed below and defined at the end of this section, are used in a descriptive sense only and not for purposes of limitation. The practice of the present invention will employ, unless otherwise indicated, conventional techniques of botany, microbiology, tissue culture, molecular biology, chemistry, biochemistry and recombinant DNA technology, which are within the skill of the art (47, 65, 76, 116, 122, 176, 187, 190).

A suitable polynucleotide for use in accordance with the invention may be obtained by cloning techniques using cDNA or genomic libraries, DNA, or cDNA from bacteria which are available commercially or which may be constructed using standard methods known to persons of ordinary skill in the art. Suitable nucleotide sequences may be isolated from DNA libraries obtained from a wide variety of species by means of nucleic acid hybridization or amplification methods, such as polymerase chain reaction (PCR) procedures, using as probes or primers nucleotide sequences selected in accordance with the invention.

Furthermore, nucleic acid sequences may be constructed or amplified using chemical synthesis. The product of amplification is termed an amplicon. Moreover, if the particular nucleic acid sequence is of a length that makes chemical synthesis of the entire length impractical, the sequence may be broken up into smaller segments that may be synthesized and ligated together to form the entire desired sequence by methods known in the art. Alternatively, individual components or DNA fragments may be amplified by PCR and adjacent fragments can be amplified together using, for example, fusion-PCR (202) or overlap-PCR (203) by methods known in the art.

A suitable polynucleotide for use in accordance with the invention may be constructed by recombinant DNA technology, for example, by cutting or splicing nucleic acids using restriction enzymes and mixing with a cleaved (cut with a restriction enzyme) vector with the cleaved insert (DNA of the invention) and ligated using DNA ligase. Alternatively amplification techniques, such as PCR, can be used, where restriction sites are incorporated in the primers that otherwise match the nucleotide sequences (especially at the 3' ends) selected in accordance with the invention. The desired amplified recombinant molecule is cut or spliced using restriction enzymes and mixed with a cleaved vector and ligated using DNA ligase. In another method, after amplification of the desired recombinant molecule, DNA linker sequences are ligated to the 5' and 3' ends of the desired nucleotide insert with ligase, the DNA insert is cleaved with a restriction enzyme that specifically recognizes sequences present in the linker sequences and the desired vector. The cleaved vector is mixed with the cleaved insert, and the two fragments are ligated using DNA ligase. In yet another method, the desired recombinant molecule is amplified with primers that have recombination sites (e.g. Gateway) incorporated in the primers, that otherwise match the nucleotide sequences selected in accordance with the invention. The desired amplified recombinant molecule is mixed with a vector containing the recombination site and recombinase, the two molecules are ligated together by recombination.

The recombinant expression cassette or DNA construct includes a promoter that directs transcription in a plant cell, operably linked to the polynucleotide encoding a bPBP or a peptide domain that is functionally similar to the bPBPs. In various aspects of the invention described herein, a variety of different types of promoters are described and used. As used herein, a polynucleotide is "operably linked" to a promoter or other nucleotide sequence when it is placed into a functional relationship with the promoter or other nucleotide sequence. The functional relationship between a promoter and a desired polynucleotide insert typically involves the polynucleotide and the promoter sequences being contiguous such that transcription of the polynucleotide sequence will be facilitated. Two nucleic acid sequences are further said to be operably linked if the nature of the linkage between the two sequences does not (1) result in the introduction of a frame-shift mutation; (2) interfere with the ability of the promoter region sequence to direct the transcription of the desired nucleotide sequence, or (3) interfere with the ability of the desired nucleotide sequence to be transcribed by the promoter sequence region. Typically, the promoter element is generally upstream (i.e., at the 5' end) of the nucleic acid insert coding sequence.

While a promoter sequence can be ligated to a coding sequence prior to insertion into a vector, in other embodiments, a vector is selected that includes a promoter operable in the host cell into which the vector is to be inserted. In addition, certain preferred vectors have a region that codes a ribosome binding site positioned between the promoter and the site at which the DNA sequence is inserted so as to be operatively associated with the DNA sequence of the invention to produce the desired polypeptide, i.e., the DNA sequence of the invention in-frame.

Suitable Promoters

A wide variety of promoters are known to those of ordinary skill in the art as are other regulatory elements that can be used alone or in combination with promoters. A wide variety of promoters that direct transcription in plants cells can be used in connection with the present invention. For purposes of describing the present invention, promoters are divided into two types, namely, constitutive promoters and non-constitutive promoters. Constitutive promoters are classified as providing for a range of constitutive expression. Thus, some are weak constitutive promoters, and others are strong constitutive promoters. Non-constitutive promoters include tissue-preferred promoters, tissue-specific promoters, cell-type specific promoters, and inducible-promoters.

Of particular interest in certain embodiments of the present invention are inducible-promoters that respond to various forms of environmental stresses, or other stimuli, including, for example, mechanical shock, heat, cold, salt, flooding, drought, salt, anoxia, pathogens, such as bacteria, fungi, and viruses, and nutritional deprivation, including deprivation during times of flowering and/or fruiting, and other forms of plant stress. For example, the promoter selected in alternate forms of the invention, can be a promoter is induced by one or more, but not limiting to one of the following, abiotic stresses such as wounding, cold, desiccation, ultraviolet-B (186), heat shock (169) or other heat stress, drought stress or water stress. The promoter may further be one induced by biotic stresses including pathogen stress, such as stress induced by a virus (173) or fungi (30, 54), stresses induced as part of the plant defense pathway (118) or by other environmental signals, such as light (139), carbon dioxide (111, 112), hormones or other signaling molecules such as auxin, hydrogen peroxide and salicylic acid (19, 23), sugars and gibberellin (120) or abscissic acid and ethylene (119).

In other embodiments of the invention, tissue-specific promoters are used. Tissue-specific expression patterns as controlled by tissue- or stage-specific promoters that include, but is not limited to, fiber-specific, green tissue-specific, root-specific, stem-specific, and flower-specific. Examples of the utilization of tissue-specific expression includes, but is not limit to, the expression in leaves of the desired peptide for the protection of plants against foliar pathogens, the expression in roots of the desired peptide for the protection of plants against root pathogens, and the expression in roots or seedlings of the desired peptide for the protection of seedlings against soil-borne pathogens. In many cases, however, protection against more than one type of pathogen may be sought, and expression in multiple tissues will be desirable.

Although many promoters from dicotyledons have been shown to be operational in monocotyledons and vice versa, ideally dicotyledonous promoters are selected for expression in dicotyledons, and monocotyledonous promoters are selected for expression in monocotyledons. There are also promoters that control expression of genes in green tissue or for genes involved in photosynthesis from both monocotyledons and dicotyledons such as the maize from the phosphenol carboxylase gene (91). There are suitable promoters for root specific expression (44, 92). A promoter selected can be an endogenous promoter, i.e. a promoter native to the species and or cell type being transformed. Alternatively, the promoter can be a foreign promoter, which promotes transcription of a length of DNA of viral, microbes, bacterial or eukaryotic origin, invertebrates, vertebrates including those from plants and plant viruses. For example, in certain preferred embodiments, the promoter may be of viral origin, including a cauliflower mosaic virus promoter (CaMV), such as CaMV 35S or19S, a figwort mosaic virus promoter (FMV 35S), or the coat protein promoter of tobacco mosaic virus (TMV). The promoter may further be, for example, a promoter for the small subunit of ribulose-1,3-biphosphate carboxylase. Promoters of bacterial origin include the octopine synthase promoter, the nopaline synthase promoter and other promoters derived from native Ti plasmids could also be (79).

The promoters may further be selected such that they require activation by other elements known to those of ordinary skill in the art, so that production of the protein encoded by the nucleic acid sequence insert may be regulated as desired. In one embodiment of the invention, a DNA construct comprising a non-constitutive promoter operably linked to a polynucleotide encoding the desired polypeptide of the invention is used to make a transformed plant that selectively increases the level of the desired polypeptide of the invention in response to a signal. The term “signal” is used to refer to a condition, stress or stimulus that results in or causes a non-constitutive promoter to direct expression of a coding sequence operably linked to it. To make such a plant in accordance with the invention, a DNA construct is provided that includes a non-constitutive promoter operably linked to a polynucleotide encoding the desired polypeptide of the invention. The construct is incorporated into a plant genome to provide a transformed plant that expresses the polynucleotide in response to a signal.

In alternate embodiments of the invention, the selected promoter is a tissue-preferred promoter, a tissue-specific promoter, a cell-type-specific promoter, an inducible promoter or other type of non-constitutive promoter. It is readily apparent that such a DNA construct causes a plant transformed thereby to selectively express the gene for the desired polypeptide of the invention. Therefore under specific conditions or in certain tissue- or cell-types the desired polypeptide will be expressed. The result of this expression in the plant depends upon the activity of the promoter and in some cases the conditions of the cell or cells in which it is expressed.

It is understood that the non-constitutive promoter does not continuously produce the transcript or RNA of the invention. But in this embodiment the selected promoter for inclusion of the invention advantageously induces or increases transcription of gene for the desired polypeptide of the invention in response to a signal, such as an environmental cue or other stress signal including biotic and/or abiotic stresses or other conditions.

In another embodiment of the invention, a DNA construct comprising a plant glutamate receptor promoter operably linked to polynucleotides that encode the desired polypeptide of the invention is used to make a transformed plant that selectively increases the transcript or RNA of the desired polypeptide of the invention in the same cells, tissues, and under the environmental conditions that express a plant glutamate receptor. It is understood to those of ordinary skill in the art that the regulatory sequences that comprise a plant promoter driven by RNA polymerase II reside in the region approximately 2900 to 1200 basepairs up-stream (5') of the translation initiation site or start codon (ATG). For example, the full-length promoter for the nodule-enhanced PEP carboxylase from alfalfa is 1277 basepairs prior to the start codon (148), the full-length promoter for cytokinin oxidase from orchid is 2189 basepairs prior to the start codon (198), the full-length promoter for ACC oxidase from peach is 2919 basepairs prior to the start codon (131), full-length promoter for cytokinin oxidase from orchid is 2189 basepairs prior to the start codon, full-length promoter for glutathione peroxidase 1 from *Citrus sinensis* is 1600 basepairs prior to the start codon (9), and the full-length promoter for glucuronosyltransferase from cotton is 1647 basepairs prior to the start codon (194). Most full-length promoters are 1700 basepairs prior to the start codon. The accepted convention is to describe this region (promoter) as −1700 to −1, where the numbers designate the number of basepairs prior to the “A” in the start codon. In this embodiment of the invention that the region of −2000 to −1 basepairs 5' to a plant glutamate receptor is operably linked to a polynucleotide for the said encoded peptide to make a transformed plant that selectively expresses the polynucleotide or increases the level of the said protein where the plant glutamate receptor is expressed or accumulates. A plant glutamate receptor promoter is the −2000 to −1 basepair region genes that include, but is not limit to, the 20 *Arabidopsis thaliana* glutamate receptors (AtGLRs or AtGluRs) and 23 rice glutamate receptors. The promoters for the following AtGLRs genes, 1.1, 2.1, 3.1, (24) 3.2 (note this is designated as GLR2 in the manuscript; 105), and 3.4 (130) have been shown to control specific cell-type, tissue-type, developmental and environmental expression patterns in plants. Those of ordinary skill in the art can either digest the desired region using restriction enzymes and ligase to clone the plant glutamate promoters or use amplification, such as PCR, techniques with the incorporation of restriction or recombination sites to clone the plant glutamate receptor promoters 5' to the desired polynucleotide. A plant glutamate receptor promoter for these purposes normally means the following regions upstream (5') to the start codon between −200 to −1 basepairs, preferably at least between −500 to −1 basepairs, preferably at least between −1000 to −1 basepairs, more preferably at least between −1500 to −1 basepairs, and most preferably at −2000 to −1 basepairs.

Suitable Vectors

A wide variety of vectors may be employed to transform a plant, plant cell or other cells with a construct made or selected in accordance with the invention, including high- or low-copy number plasmids, phage vectors and cosmids. Such vectors, as well as other vectors, are well known in the art. Representative T-DNA vector systems (6, 79) and numerous expression cassettes and vectors and in vitro culture methods for plant cell or tissue transformation and regeneration of plants are known and available (74). The vectors can be chosen such that operably linked promoter and polynucleotides that encode the desired polypeptide of the invention are incorporated into the genome of the plant. Although the preferred embodiment of the invention is expression in plants or plant cells, other embodiments may include expression in prokaryotic or eukaryotic photosynthetic organisms, microbes, invertebrates or vertebrates.

It is known by those of ordinary skill in the art that there exist numerous expression systems available for expression of a nucleic acid encoding a fusion protein of the present invention. There are many commercially available recombinant vectors to transform a host plant or plant cell. Standard molecular and cloning techniques (8, 122, 190) are available to make a recombinant expression cassette that expresses the polynucleotide that encodes the desired polypeptide of the invention. No attempt to describe in detail the various methods known for the expression of proteins in prokaryotes or eukaryotes will be made. In brief, the expression of isolated nucleic acids encoding a fusion protein of the present invention will typically be achieved by operably linking, for example, the DNA or cDNA to a promoter, followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding a protein of the present invention. To obtain high-level expression of a cloned gene, it is desirable to construct expression vectors that contain, at the minimum, a strong promoter, such as ubiquitin, to direct transcription, a ribosome-binding site for translational initiation, and a transcription/translation terminator.

One of ordinary skill to the art recognizes that modifications could be made to a fusion protein of the present invention without diminishing its biological activity. Some modifications may be made to facilitate the cloning, expression, targeting or to direct the location of the polypeptide in the host, or for the purification or detection of the polypeptide by the addition of a “tag” as a fusion protein. Such modifications are well known to those of skill in the art and include, for example, a methionine added at the amino terminus to provide an initiation site, additional amino acids (tags) placed on either terminus to create a tag, additional nucleic acids to insert a restriction site or a termination.

In addition to the selection of a suitable promoter, the DNA constructs requires an appropriate transcriptional terminator to be attached downstream of the desired gene of the invention for proper expression in plants. Several such terminators are available and known to persons of ordinary skill in the art. These include, but are not limited to, the tml from CaMV and E9 from rbcS. Another example of a terminator sequence is the polyadenylation sequence from the bovine growth hormone gene. A wide variety of available terminators known to function in plants can be used in the context of this invention. Vectors may also have other control sequence features that increase their suitability. These include an origin of replication, enhancer sequences, ribosome binding sites, RNA splice sites, polyadenylation sites, selectable markers and RNA stability signal. Origin of replication is a gene sequence that controls replication of the vector in the host cell. Enhancer sequences cooperate with the promoter to increase expression of the polynucleotide insert coding sequence. Enhancers can stimulate promoter activity in host cell. An example of specific polyadenylation sequence in higher eukaryotes is ATTTA. Examples of plant polyadenylation signal sequences are AATAAA or AATAAT. RNA splice sites are sequences that ensure accurate splicing of the transcript. Selectable markers usually confer resistance to an antibiotic, herbicide or chemical or provide color change, which aid the identification of transformed organisms. The vectors also include a RNA stability signal, which are 3'-regulatory sequence elements that increase the stability of the transcribed RNA (138, 142).

In addition, polynucleotides that encode the bPBP or a peptide domain from a prokaryotic and eukaryotic protein that is functionally similar to the bPBPs can be placed in the appropriate plant expression vector used to transform plant cells. The fusion protein can then be isolated from plant callus or the transformed cells can be used to regenerate transgenic plants. Such transgenic plants can be harvested, and the appropriate tissues can be subjected to large-scale protein extraction and purification techniques.

The vectors may include another polynucleotide insert that encodes a peptide or polypeptide used as a “tag” to aid in purification or detection of the desired protein. The additional polynucleotide is positioned in the vector such that upon cloning and expression of the desired polynucleotide a fusion, or chimeric, protein is obtained. The tag may be incorporated at the amino or carboxy terminus. If the vector does not contain a tag, persons with ordinary skill in the art know that the extra nucleotides necessary to encode a tag can be added with the ligation of linkers, adaptors, or spacers or by PCR using designed primers. After expression of the peptide the tag can be used for purification using affinity chromatography, and if desired, the tag can be cleaved with an appropriate enzyme. The tag can also be maintained, not cleaved, and used to detect the accumulation of the desired polypeptide in the protein extracts from the host using western blot analysis. In another embodiment, a vector includes the polynucleotides for the tag that is fused in-frame to the polynucleotides that encodes a functional bPBP or a domain from a prokaryotic and eukaryotic protein that is functionally similar to the bPBPs to form a fusion protein. The tags that may be used include, but are not limited to, Arg-tag, calmodulin-binding peptide, cellulose-binding domain, DsbA, c-myc-tag, glutathione S-transferase, FLAG-tag, HAT-tag, His-tag, maltose-binding protein, NusA, S-tag, SBP-tag, Strep-tag, and thioredoxin (Trx-Tag). These are available from a variety of manufacturers Clontech Laboratories, Takara Bio Company GE Healthcare, Invitrogen, Novagen Promega and QIAGEN.

The vector may include another polynucleotide that encodes a signal polypeptide or signal sequence to direct the desired fusion protein in the host cell, so that the fusion protein accumulates in a specific cellular compartment, subcellular compartment, or membrane. The specific cellular compartments include the apoplast, vacuole, plastids chloroplast, mitochondrion, peroxisomes, secretory pathway, lysosome, endoplasmic reticulum, nucleus or Golgi apparatus. In addition, a signal polypeptide or signal sequence can be used to direct the fusion proteins to specific membranes include, but are not limited to, the inner or outer mitochondrial membrane, inner or outer chloroplast membrane, inner or outer nuclear membrane, vacuolar membrane (tonoplast), plasma membrane, endomembrane system including the endoplasmic reticulum and Golgi apparatus, glyoxysomal membrane, peroxisomal membrane, lysosomal membrane, or membranes associated with plastids including proplastids etioplasts, and chromoplasts. A signal polypeptide or signal sequence is usually at the N terminus and normally absent from the mature protein due to protease that removes the signal peptide when the polypeptide reaches its final destination. Signal sequences can be a primary sequence located at the N-terminus (158, 174, 180, 188), C-terminus (70, 71) or internal (29, 77, 128) or tertiary structure (77). If a signal polypeptide or signal sequence to direct the polypeptide does not exist on the vector, it is expected that those of ordinary skill in the art can incorporate the extra nucleotides necessary to encode a signal polypeptide or signal sequence by the ligation of the appropriate nucleotides or by PCR. Those of ordinary skill in the art can identify the nucleotide sequence of a signal polypeptide or signal sequence using computational tools. There are numerous computational tools available for the identification of targeting sequences or signal sequence. These include, but are not limited to, TargetP (51, 52), iPSORT (11), SignalP (14), PrediSi (83), ELSpred (17) HSLpred (67) and PSLpred (16), MultiLoc (86), SherLoc (164), ChloroP (53), MITOPROT (27), Predotar (170) and 3D-PSSM (103). Additional methods and protocols are discussed in the literature (86).

Transformation of Host Cells

Transformation of a plant can be accomplished in a wide variety of ways within the purview of a person of ordinary skill in the art. In one embodiment, a DNA construct is incorporated into a plant by (i) transforming a cell, tissue or organ from a host plant with the DNA construct; (ii) selecting a transformed cell, cell callus, somatic embryo, or seed which contains the DNA construct; (iii) regenerating a whole plant from the selected transformed cell, cell callus, somatic embryo, or seed; and (iv) selecting a regenerated whole plant that expresses the polynucleotide. Many methods of transforming a plant, plant tissue or plant cell for the construction of a transformed cell are suitable. Once transformed, these cells can be used to regenerate transgenic plants (163).

Those of ordinary skill in the art can use different plant gene transfer techniques found in references for, but not limited to, the electroporation (42, 63, 64, 117, 155), microinjection (39, 72), lipofection (175), liposome or spheroplast fusions (26, 46, 141), *Agrobacterium* (88), direct gene transfer (147), T-DNA mediated transformation of monocots (87), T-DNA mediated transformation of dicots (15, 156), microprojectile bombardment or ballistic particle acceleration (107, 108, 127, 159), chemical transfection including $CaCl_2$ precipitation, polyvinyl alcohol, or poly-L-ornithine (62), silicon carbide whisker methods (61, 181), laser methods (10, 75), sonication methods (5, 12, 59), polyethylene glycol methods (110), vacuum infiltration (13), and transbacter (201).

In one embodiment of the invention, a transformed host cell may be cultured to produce a transformed plant. In this regard, a transformed plant can be made, for example, by transforming a cell, tissue or organ from a host plant with an inventive DNA construct; selecting a transformed cell, cell callus, somatic embryo, or seed which contains the DNA construct; regenerating a whole plant from the selected transformed cell, cell callus, somatic embryo, or seed; and selecting a regenerated whole plant that expresses the polynucleotide.

A wide variety of host cells may be used in the invention, including prokaryotic and eukaryotic host cells. These cells or organisms may include microbes, invertebrate, vertebrates or photosynthetic organisms. Preferred host cells are eukaryotic, preferably plant cells, such as those derived from monocotyledons, such as duckweed, corn, rye grass, Bermuda grass, Blue grass, Fescue, or dicotyledons, including lettuce, cereals such as wheat, rapeseed, radishes and cabbage, green peppers, potatoes and tomatoes, and legumes such as soybeans and bush beans.

Plant Host Cells

The methods described above may be applied to transform a wide variety of plants, including decorative or recreational plants or crops, but are particularly useful for treating commercial and ornamental crops. Examples of plants that may be transformed in the present invention include, but are not limited to, *Acacia*, alfalfa, aneth, apple, apricot, artichoke, arugula, asparagus, avocado, banana, barley, beans, beech, beet, Bermuda grass, blackberry, blueberry, Blue grass, broccoli, Brussels sprouts, cabbage, camelina, canola, cantaloupe, carrot, cassava, cauliflower, celery, cherry, chicory, cilantro, citrus, clementines, coffee, corn, cotton, cucumber, duckweed, Douglas fir, eggplant, endive, escarole, eucalyptus, fennel, fescue, figs, forest trees, garlic, gourd, grape, grapefruit, honey dew, jatropha, jicama, kiwifruit, lettuce, leeks, lemon, lime, Loblolly pine, maize, mango, melon, mushroom, nectarine, nut, oat, okra, onion, orange, an ornamental plant, palm, papaya, parsley, pea, peach, peanut, pear, pepper, persimmon, pine, pineapple, plantain, plum, pomegranate, poplar, potato, pumpkin, quince, radiata pine, radicchio, radish, rapeseed, raspberry, rice, rye, rye grass, scallion, sorghum, Southern pine, soybean, spinach, squash, strawberry, sugarbeet, sugarcane, sunflower, sweet potato, sweetgum, switchgrass, tangerine, tea, tobacco, tomato, turf, turnip, a vine, watermelon, wheat, yams, and zucchini. Other suitable hosts include bacteria, fungi, algae and other photosynthetic organisms, and animals including vertebrate and invertebrates.

Once transformed, the plant may be treated with other "active agents" either prior to or during the exposure of the plant to stress to further decrease the effects of plant stress. "Active agent" as used herein refers to an agent that has a beneficial effect on the plant or increases production of amino acid production by the plant. For example, the agent may have a beneficial effect on the plant with respect to nutrition, and the resistance against, or reduction of, the effects of plant stress. Some of these agents may be amino acids that act as ligands or agonists to the bPBPs or to domains from prokaryotic and eukaryotic proteins that are functionally similar to the bPBPs. The increased binding could promote growth, development, biomass and yield, and change in metabolism. In addition to the twenty amino acids that are involved in protein synthesis, other non-protein amino acids, such as GABA, citrulline, and ornithine, or other nitrogen containing compounds such as polyamines may also be used to activate the bPBP(s) or domains from prokaryotic and eukaryotic proteins that are functionally similar to the bPBPs. Depending on the type of gene construct or recombinant expression cassette, other metabolites and nutrients may be used to activate the bPBP(s) or domains from prokaryotic and eukaryotic proteins that are functionally similar to the bPBPs. These include, but are not limited to, sugars, carbohydrates, lipids, oligopeptides, mono-(glucose, arabinose, fructose, xylose, and ribose) di-(sucrose and trehalose) and polysaccharides, carboxylic acids (succinate, malate and fumarate) and nutrients such as phosphate, molybdate, or iron.

Accordingly, the active agent may include a wide variety of fertilizers, pesticides and herbicides known to those of ordinary skill in the art (106). Other greening agents fall within the definition of "active agent" as well, including minerals such as calcium, magnesium and iron. The pesticides protect the plant from pests or disease and may be either chemical or biological and include fungicides, bactericides, insecticides and anti-viral agents as known to those of ordinary skill in the art.

Prokaryotic Host Cells

The use of prokaryotes as hosts includes strains of *E. coli*. However, other microbial strains including, but not limited to, *Bacillus* (132) and *Salmonella* may also be used. Commonly used prokaryotic control sequences include promoters for transcription initiation, optionally with an operator, along with ribosome binding site sequences. Commonly used prokaryotic promoters include the beta lactamase (18), lactose (18), and tryptophan (68) promoters. The vectors usually contain selectable markers to identify transfected or transformed cells. Some commonly used selectable markers include the genes for resistance to ampicillin, tetracycline, or chloramphenicol. The vectors are typically a plasmid or phage. Bacterial cells are transfected or transformed with the plasmid vector DNA. Phage DNA can be infected with phage vector particles or transfected with naked phage DNA. The plasmid and phage DNA for the vectors are commercially available from numerous vendors known to those of ordinary skill in the art.

Non-Plant Eukaryotic Host Cells

Fusion proteins of the present invention can be expressed in a variety of eukaryotic expression systems such as yeast, insect cell lines, and mammalian cells which are known to those of ordinary skill in the art. For each host system there are suitable vectors that are commercially available (e.g., Invitrogen, Startagene, GE Healthcare Life Sciences). The vectors usually have expression control sequences, such as promoters, an origin of replication, enhancer sequences, termination sequences, ribosome binding sites, RNA splice sites, polyadenylation sites, transcriptional terminator sequences, and selectable markers. Synthesis of heterologous proteins in yeast is well known to those of ordinary skill in the art (167, 168). The most widely used yeasts are *Saccharomyces cerevisiae* and *Pichia pastoris*. Insect cell lines that include, but are not limited to, mosquito larvae, silkworm, armyworm, moth, and *Drosophila* cell lines can be used to express proteins of the present invention using baculovirus-derived vectors. Mammalian cell systems often will be in the form of monolayers of cells although mammalian cell suspensions may also be used. A number of suitable host cell lines capable of expressing intact proteins have been developed in the art, and include the HEK293, BHK21, and CHO cell lines.

A fusion protein of the present invention, once expressed in any of the non-plant eukaryotic systems can be isolated from the organism by lysing the cells and applying standard protein isolation techniques to the lysates or the pellets. The monitoring of the purification process can be accomplished by using western blot techniques or radioimmunoassay of other standard immunoassay techniques.

DEFINITIONS

Unless defined otherwise, all technical and scientific terms used herein have the same meaning as is commonly understood by one of skill in the art to which the invention belongs.

The term "polynucleotide" refers to a natural or synthetic linear and sequential array of nucleotides and/or nucleosides, including deoxyribonucleic acid, ribonucleic acid, and derivatives thereof. It includes chromosomal DNA, self-replicating plasmids, infectious polymers of DNA or RNA and DNA or RNA that performs a primarily structural role. Unless otherwise indicated, nucleic acids or polynucleotide are written left to right in 5' to 3' orientation, Nucleotides are referred to by their commonly accepted single-letter codes. Numeric ranges are inclusive of the numbers defining the range.

The terms "amplified" and "amplification" refer to the construction of multiple copies of a nucleic acid sequence or multiple copies complementary to the nucleic acid sequence using at least one of the nucleic acid sequences as a template. Amplification can be achieved by chemical synthesis using any of the following methods, such as solid-phase phosphoramidate technology or the polymerase chain reaction (PCR). Other amplification systems include the ligase chain reaction system, nucleic acid sequence based amplification, Q-Beta Replicase systems, transcription-based amplification system, and strand displacement amplification. The product of amplification is termed an amplicon.

As used herein "promoter" includes reference to a region of DNA upstream from the start of transcription and involved in recognition and binding of RNA polymerase, either I, II or III, and other proteins to initiate transcription. Promoters include necessary nucleic acid sequences near the start site of transcription, such as, in the case of a polymerase II type promoter, a TATA element. A promoter also optionally includes distal enhancer or repressor elements, which can be located as far as several thousand base pairs from the start site of transcription.

The term "plant promoter" refers to a promoter capable of initiating transcription in plant cells.

The term "animal promoter" refers to a promoter capable of initiating transcription in animal cells.

The term "microbe promoter" refers to a promoter capable of initiating transcription in microbes.

The term "foreign promoter" refers to a promoter, other than the native, or natural, promoter, which promotes transcription of a length of DNA of viral, bacterial or eukaryotic origin, including those from microbes, plants, plant viruses, invertebrates or vertebrates.

The term "microbe" refers to any microorganism (including both eukaryotic and prokaryotic microorganisms), such as fungi, yeast, bacteria, actinomycetes, algae and protozoa, as well as other unicellular structures.

The term "plant" includes whole plants, and plant organs, and progeny of same. Plant organs comprise, e.g., shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit (the mature ovary), plant tissue (e.g. vascular tissue, ground tissue, and the like) and cells (e.g. guard cells, egg cells, trichomes and the like). The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid and hemizygous.

The term "constitutive" refers to a promoter that is active under most environmental and developmental conditions, such as, for example, but not limited to, the CaMV 35S promoter and the nopaline synthase terminator.

The term "tissue-preferred promoter" refers to a promoter that is under developmental control or a promoter that preferentially initiates transcription in certain tissues.

The term "tissue-specific promoter" refers to a promoter that initiates transcription only in certain tissues.

The term "cell-type specific promoter" refers to a promoter that primarily initiates transcription only in certain cell types in one or more organs.

The term "inducible promoter" refers to a promoter that is under environmental control.

The terms "encoding" and "coding" refer to the process by which a polynucleotide, through the mechanisms of transcription and translation, provides the information to a cell from which a series of amino acids can be assembled into a specific amino acid sequence to produce a functional polypeptide, such as, for example, an active enzyme or ligand binding protein.

The terms "polypeptide," "peptide," and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers Amino acids may be referred to by their commonly known three-letter or one-letter symbols Amino acid sequences are written left to right in amino to carboxy orientation, respectively. Numeric ranges are inclusive of the numbers defining the range.

The terms "residue," "amino acid residue," and "amino acid" are used interchangeably herein to refer to an amino acid that is incorporated into a protein, polypeptide, or peptide. The amino acid may be a naturally occurring amino acid and may encompass known analogs of natural amino acids that can function in a similar manner as the naturally occurring amino acids.

The terms "bacterial periplasmic binding protein" and "bPBP" refer to a class or group of proteins with a tertiary structure that forms a lobe-hinge-lobe region, or two lobes, that bind to a ligand, agonist or antagonist by a Venus-flytrap mechanism. Proteins in this group include those found in the periplasmic binding proteins-like I, periplasmic binding proteins-like II, proteins with a LIVBP-LD, proteins with a LAOBP-LD and proteins in the superfamily of extracellular or periplasmic solute-binding proteins, families 1 through 8.

The term "domains from prokaryotic and eukaryotic proteins that are functionally similar to the bPBPs" refers to portions of proteins from bacteria or eukaryotes with a tertiary structure that forms a lobe-hinge-lobe region, or two lobes, that bind to a ligand, agonist or antagonist by a Venus flytrap mechanism. Proteins in this group include proteins with a LIVBP-LD or LAOBP-LD such as those found in bacterial glutamate receptors, vertebrate or invertebrate inotropic glutamate receptor, plant glutamate receptors, members of family C of G-protein coupled receptors and atrial natriuretic peptide receptors.

The terms "functional" and "functionally," with reference to functional bPBP or domains from prokaryotic and eukaryotic proteins that are functionally similar to the bPBPs, refer to a protein or portions of protein from the above mentioned prokaryotic or eukaryotic gene or protein families that have a tertiary structure that forms a lobe-hinge-lobe region, or two lobes, that bind to a ligand, agonist or antagonist by a Venus-flytrap mechanism.

The term "ligand" refers to the specific molecule that binds in the cell to the bPBP or domains from prokaryotic and eukaryotic proteins that are functionally similar to the bPBPs. Ligands are very diverse, and they range from simple molecules like metals to complex molecules like oligopeptides or oligosaccharides. In addition, the ligands include various types of molecules such as amino acids, sugars, carboxylic acids and polyamines.

The term "agonist" refers to specific molecules that bind to the bPBP or domains from prokaryotic and eukaryotic proteins that are functionally similar to the bPBPs and mimics the ligand.

The term "antagonist" refers to specific molecules that bind to the bPBP or domains from prokaryotic and eukaryotic proteins that are functionally similar to the bPBPs and blocks or prevents ligand binding.

The terms "transmembrane domain" or "transmembrane region" are used interchangeably herein to refer to a polypeptide of 19 to 25 amino acid residues in length that contains mostly hydrophobic amino acids that form an alpha helix that is located in a membrane. The membrane can be the plasma membrane, peroxisomal or glyoxysomal membrane, lysosomal membrane, vacuolar membrane or tonoplast, or a part of the membranes associated with and in the plastid, chloroplast, mitochondrion, nucleus or endomembrane system.

The term "membrane" refers to a lipid bilayer that separates cells, cellular structures or subcellular organelles. This includes, but is not limited to, the plasma membrane or outer cellular membrane, vacuolar membrane (tonoplast), endomembrane system including the endoplasmic reticulum and Golgi apparatus, glyoxysomal membrane, peroxisomal membrane, inner or outer chloroplast membrane, inner or outer nuclear membrane, inner or outer mitochondrial membrane lysosomal membrane, or membranes associated with plastids including proplastids etioplasts, and chromoplasts The term "truncated metabolic regulator protein" refers to a metabolic regulator protein that has been truncated by removal of amino acids from the N terminus of the protein without affecting the ability of the truncated metabolic regulator peptide from binding with specific metabolites. Preferably, the amino acids of the signal peptide has been removed from the N terminus of the metabolic regulator protein.

The term "recombinant" includes reference to a cell or vector that has been modified by the introduction of a heterologous nucleic acid. Recombinant cells express genes that are not normally found in that cell or express native genes that are otherwise abnormally expressed, underexpressed, or not expressed at all as a result of deliberate human intervention, or expression of the native gene may have reduced or eliminated as a result of deliberate human intervention.

The term "recombinant expression cassette" refers to a nucleic acid construct, generated recombinantly or synthetically, with a series of specified nucleic acid elements, which permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The term "transgenic plant" includes reference to a plant, which comprises within its genome a heterologous polynucleotide. Generally, the heterologous polynucleotide is integrated within the genome such that the polynucleotide is passed on to successive generations. The heterologous polynucleotide may be integrated into the genome alone or as part of a recombinant expression cassette. "Transgenic" is also used to include any cell, cell line, callus, tissue, plant part or plant, the genotype of which has been altered by the presence of heterologous nucleic acid including those transgenic plants altered or created by sexual crosses or asexual propagation from the initial transgenic plant. The term "transgenic" does not encompass the alteration of the genome by conventional plant breeding methods or by naturally occurring events such as random cross-fertilization, non-recombinant viral infection, non-recombinant bacterial transformation, non-recombinant transposition, or spontaneous mutation.

The term "vector" includes reference to a nucleic acid used in transfection or transformation of a host cell and into which can be inserted a polynucleotide.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 40% sequence identity, preferably 60-90% sequence identity, and most preferably 100% sequence identity (i.e., complementary) with each other.

The terms "stringent conditions" and "stringent hybridization conditions" include reference to conditions under which a probe will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which can be up to 100% complementary to the probe (homologous probing). Alternatively, stringency conditions can be adjusted to allow some mismatching in sequences so that lower degrees of similarity are detected (heterologous probing). Optimally, the probe is approximately 500 nucleotides in length, but can vary greatly in length from less than 500 nucleotides to equal to the entire length of the target sequence.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide or Denhardt's. Low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Moderate stringency conditions include hybridization in 40 to 45% formamide, 1 M NaCl, 1% SDS at 37° C., and a wash in 0.5× to 1×SSC at 55 to 60° C. High stringency conditions include hybridization in 50% formamide, 1 M NaCl, 1% SDS at 37° C., and a wash in 0.1×SSC at 60 to 65° C. Specificity is typically the function of post-hybridization washes, the critical factors being the ionic strength and temperature of the final wash solution. For DNA-DNA hybrids, the $T_m$ can be approximated (129), where the $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3 or 4° C. lower than the thermal melting point ($T_m$); moderately stringent conditions can utilize a hybridization and/or wash at 6, 7, 8, 9 or 10° C. lower than the thermal melting point ($T_m$); low stringency conditions can utilize a hybridization and/or wash at 11, 12, 13, 14, 15 or 20° C. lower than the thermal melting point ($T_m$). Using the equation, hybridization and wash compositions, and desired $T_m$, those of ordinary skill in the art will understand that variations in the stringency of hybridization and/or wash solutions are inherently described. An extensive guide to the hybridization of nucleic acids is found in the scientific literature (8, 182) Unless otherwise stated, in the present application high stringency is defined as hybridization in 4×SSC, 5×Denhardt's (5 g Ficoll, 5 g polyvinylpyrrolidone, 5 g bovine serum albumin in 500 ml of water), 0.1 mg/ml boiled salmon sperm DNA, and 25 mM Na phosphate at 65° C., and a wash in 0.1×SSC, 0.1% SDS at 65° C.

The following terms are used to describe the sequence relationships between two or more nucleic acids or polynucleotides or polypeptides: "reference sequence," "comparison window," "sequence identity," "percentage of sequence identity," and "substantial identity."

The term "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

The term "comparison window" includes reference to a contiguous and specified segment of a polynucleotide sequence, where the polynucleotide sequence may be compared to a reference sequence and the portion of the polynucleotide sequence in the comparison window may comprise additions or deletions (i.e., gaps) when it is compared to the reference sequence for optimal alignment. The comparison window is usually at least 20 contiguous nucleotides in length, and optionally can be 30, 40, 50, 100 or longer. Those of ordinary skill in the art understand that the inclusion of gaps in a polynucleotide sequence alignment introduces a gap penalty, and it is subtracted from the number of matches.

Methods of alignment of nucleotide and amino acid sequences for comparison are well known to those of ordinary skill in the art. The local homology algorithm, BESTFIT, (172) can perform an optimal alignment of sequences for comparison using a homology alignment algorithm called GAP (137), search for similarity using Tfasta and Fasta (149), by computerized implementations of these algorithms widely available on-line or from various vendors (Intelligenetics, Genetics Computer Group). CLUSTAL allows for the alignment of multiple sequences (80, 81, 82) and program PileUp can be used for optimal global alignment of multiple sequences (56). The BLAST family of programs can be used for nucleotide or protein database similarity searches. BLASTN searches a nucleotide database using a nucleotide query. BLASTP searches a protein database using a protein query. BLASTX searches a protein database using a translated nucleotide query that is derived from a six-frame translation of the nucleotide query sequence (both strands). TBLASTN searches a translated nucleotide database using a protein query that is derived by reverse-translation. TBLASTX search a translated nucleotide database using a translated nucleotide query.

GAP (137) maximizes the number of matches and minimizes the number of gaps in an alignment of two complete sequences. GAP considers all possible alignments and gap positions and creates the alignment with the largest number of matched bases and the fewest gaps. It also calculates a gap penalty and a gap extension penalty in units of matched bases. Default gap creation penalty values and gap extension penalty values in Version 10 of the Wisconsin Genetics Software Package are 8 and 2, respectively. The gap creation and gap extension penalties can be expressed as an integer selected from the group of integers consisting of from 0 to 100. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (78).

Unless otherwise stated, sequence identity or similarity values refer to the value obtained using the BLAST 2.0 suite of programs using default parameters (3). As those of ordinary skill in the art understand that BLAST searches assume that proteins can be modeled as random sequences and that proteins comprise regions of nonrandom sequences, short repeats, or enriched for one or more amino acid residues, called low-complexity regions. These low-complexity regions may be aligned between unrelated proteins even though other regions of the protein are entirely dissimilar. Those of ordinary skill in the art can use low-complexity filter programs to reduce number of low-complexity regions that are aligned in a search. These filter programs include, but are not limited to, the SEG (192, 193) and XNU (28).

The terms "sequence identity" and "identity" are used in the context of two nucleic acid or polypeptide sequences and include reference to the residues in the two sequences, which are the same when aligned for maximum correspondence over a specified comparison window. When the percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conserved substitutions, the percent sequence identity may be adjusted upwards to correct for the conserved nature of the substitution. Sequences, which differ by such conservative substitutions, are said to have "sequence similarity" or "similarity." Scoring for a conservative substitution allows for a partial rather than a full mismatch (135), thereby increasing the percentage sequence similarity.

The term "percentage of sequence identity" means the value determined by comparing two optimally aligned sequences over a comparison window, wherein the portion of the polynucleotide sequence in the comparison window may comprise gaps (additions or deletions) when compared to the reference sequence for optimal alignment. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has between 50-100% sequence identity, preferably at least 50% sequence identity, preferably at least 60% sequence identity, preferably at least 70%, more preferably at least 80%, more preferably at least 90%, and most preferably at least 95%, compared to a reference sequence using one of the alignment programs described using standard parameters. One of ordinary skill in the art will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of between 50-100%. Another indication that nucleotide sequences are substantially identical is if two molecules hybridize to each low stringency conditions, moderate stringency conditions or high stringency conditions. Yet another indication that two nucleic acid sequences are substantially identical is if the two polypeptides immunologically cross-react with the same antibody in a western blot, immunoblot or ELISA assay.

The terms "substantial identity" in the context of a peptide indicates that a peptide comprises a sequence with between 55-100% sequence identity to a reference sequence preferably at least 55% sequence identity, preferably 60% preferably 70%, more preferably 80%, most preferably at least 90% or 95% sequence identity to the reference sequence over a specified comparison window. Preferably, optimal alignment is conducted using the homology alignment algorithm (137). Thus, a peptide is substantially identical to a second peptide, for example, where the two peptides differ only by a conserved substitution. Another indication that amino acid sequences are substantially identical is if two polypeptides immunologically cross-react with the same antibody in a western blot, immuno blot or ELISA assay. In addition, a peptide can be substantially identical to a second peptide when they differ by a non-conservative change if the epitope that the antibody recognizes is substantially identical.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, *Molecular Cloning* (Cold Spring Harbor Laboratory Press, Cold Spring Harbor, N.Y.); Sambrook et al., 1989, *Molecular Cloning,* 2nd Ed. (Cold Spring Harbor Laboratory Press, Cold Spring Harbor, N.Y.); Sambrook and Russell, 2001, *Molecular Cloning,* 3rd Ed. (Cold Spring Harbor Laboratory Press, Cold Spring Harbor, N.Y.); Ausubel et al., 1992), *Current Protocols in Molecular Biology* (John Wiley & Sons, including periodic updates); Glover, 1985, *DNA Cloning* (IRL Press, Oxford); Russell, 1984*, Molecular biology of plants: a laboratory course manual* (Cold Spring Harbor Laboratory Press, Cold Spring Harbor, N.Y.); Anand, *Techniques for the Analysis of Complex Genomes*, (Academic Press, New York, 1992); Guthrie and Fink, *Guide to Yeast Genetics and Molecular Biology* (Academic Press, New York, 1991); Harlow and Lane, 1988, *Antibodies*, (Cold Spring Harbor Laboratory Press, Cold Spring Harbor, N.Y.); *Nucleic Acid Hybridization* (B. D. Hames & S. J. Higgins eds. 1984); *Transcription And Translation* (B. D. Hames & S. J.

Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes 1-IV (D. M. Weir and C. C. Blackwell, eds., 1986); Riott, *Essential Immunology,* 6th Edition, Blackwell Scientific Publications, Oxford, 1988; Fire et al., *RNA Interference Technology: From Basic Science to Drug Development*, Cambridge University Press, Cambridge, 2005; Schepers, *RNA Interference in Practice*, Wiley-VCH, 2005; Engelke, *RNA Interference* (*RNAi*): *The Nuts & Bolts of siRNA Technology*, DNA Press, 2003; Gott, *RNA Interference, Editing, and Modification: Methods and Protocols* (*Methods in Molecular Biology*), Human Press, Totowa, N.J., 2004; Sohail, *Gene Silencing by RNA Interference: Technology and Application*, CRC, 2004.

All patents, patent applications, and references cited in this disclosure are expressly incorporated herein by reference. The above disclosure generally describes the present invention. A more complete understanding can be obtained by reference to the following specific examples, which are provided for purposes of illustration only and are not intended to limit the scope of the invention.

EXAMPLE 1

Development of a Transgenic Plant that Constitutively Expresses an Anchored Metabolic Regulator Containing a Putrescine Periplasmic Binding Protein Step 1. Prepare DNA construct Prepare a DNA construct that contains an AtTUB5 (locus tag At120010) promoter with a putrescine periplasmic binding protein (putPBP) fused to a transmembrane and a NOS terminator as follows:

Step 1a. Use PCR to amplify the AtTUB5 promoter (−1851 to −1 bps) using 500 ng of DNA from an *Arabidopsis thaliana* Col-0 lambda genomic library. Add 500 ng of the following primers: 5'EcoR1TUB5prom (5'-ttttGAATTCcacatttgcaaaatgatgaatg-3'; SEQ ID NO:1) and 3' SacTUB5prom (5'-ttttGAGCTCccaatctggttaccgcattgac-3'; SEQ ID NO:2); here and in the examples that follow, capitalized nucleotides are restriction enzyme sites introduced into the primer during its synthesis. Run the following PCR reaction: 96° C. for 5 min followed by 25 cycles of 94° C. for 45 seconds, 60° C. for 30 seconds, 70° C. for 3 min, and 72° C. for 3 min. Digest the resulting DNA fragment with SacI. Inactivate the restriction enzyme as described by the manufacturer.

Step 1b. Use PCR to amplify the putPBP using 500 ng of DNA from *E. coli* strain K12. Add 500 ng of the following primers: 5' SacputPBP (5'-ttttGAGCTCatgaaaaaatggtcacgccacc-3'; SEQ ID NO:3) and 3'KpnputPBP (5'-ttttGGTACCacgtcctgctttcagcttc-3'; SEQ ID NO:4). Run the following PCR reaction: 96° C. for 5 min followed by 25 cycles of 94° C. for 45 seconds, 60° C. for 30 seconds, 70° C. for 3 min, and 72° C. for 3 min. Digest the resulting DNA fragment with SacI and KpnI. Inactivate the restriction enzyme as described by the manufacturer.

Step 1c. Use PCR to amplify the transmembrane domain using 500 ng of DNA from a *Synechocystis* sp. strain PCC 6803 genomic library. Add 500 ng of the following primers: 5'KpnGLR0TM (5'-ttttGGTACCttttttggcatagccgctttgt-3'; SEQ ID NO:5) and 3'XbaGLR0TM (5'-ttttTCTAGAttataaccaaattaaattccccacc-3'; SEQ ID NO:6). Run the following PCR reaction: 96° C. for 5 min followed by 25 cycles of 94° C. for 45 seconds, 60° C. for 30 seconds, 70° C. for 1 min, and 72° C. for 3 min. Digest the resulting DNA fragment with KpnI and XbaI. Inactivate the restriction enzyme as described by manufacturer.

Step 1d. Use PCR to amplify the NOS terminator using 500 ng of pPV1. Add 500 ng of the following primers 5'XbaNOSterm (5'-ttttTCTAGAtaccgagctcgaatttccccga-3'; SEQ ID NO:7) and 3'PstNOSterm (5'-ttttCTGCAGgatctagtaacatagatgacac-3'; SEQ ID NO:8). Run the following PCR reaction: 96° C. for 5 min followed by 25 cycles of 94° C. for 45 seconds, 60° C. for 30 seconds, 70° C. for 3 min, and 72° C. for 3 min. Digest the resulting DNA fragment with XbaI. Inactivate the restriction enzyme as described by manufacturer.

Step 1e. Combine the digested fragments (from steps 1a, 1b, 1c, and 1d) and ligate at 4° C. overnight. Use the ligated fragment as a template for PCR to amplify the entire construct by adding 500 ng of the following primers: 5'EcoRITUB5prom and 3'PstNOSterm. Run the following PCR reaction: 96° C. for 5 min followed by 20 cycles of 94° C. for 45 seconds, 60° C. for 30 seconds, 70° C. for 5 min, and 72° C. for 3 min. Digest the resulting DNA fragment with EcoRI and PstI and ligate into the vector pCAMBIA1105.1 that has been predigested with EcoRI and PstI.

Step 1f. Transform the ligated vector containing the DNA construct by electroporation into *E. coli*. Select for spectinomycin (100 μg/ml) or streptomycin (200 μg/ml) resistance on LB plates. Confirm the presence of the DNA constructs in colonies by PCR analysis with the 5'KpnTUB5prom and 3'PstNOSterm primers using the following program: 96° C. for 3 min followed by 25 cycles of 94° C. for 30 seconds, 55° C. for 30 seconds, 72° C. for 5 min, and 72° C. for 3 min. Grow a colony that contains the proper DNA construct overnight at 37° C. in 6 ml LB plus spectinomycin (100 μg/ml) or streptomycin (200 μg/ml). Isolate the plasmid DNA that contains the DNA construct and plasmid by Wizard Plus SV Minipreps DNA Purification System (Promega Corporation, Madison, Wis., USA). Sequence the DNA insert to confirm its identity and the fidelity of the DNA construct.

Step 2. Transform *Agrobacterium tumefaciens:*

Transform the vector construct into electrocompetent *Agrobacterium tumefaciens* EHA105, as described by the Green Lab Protocol (http colon//www dot bch dot msu dot edu/pamgreen/green dot htm). Select positive transformants using Terrific Broth plus spectinomycin (100 μg/ml) or streptomycin (200 μg/ml) on 1% agar plates. Confirm *Agrobacterium* colonies by PCR using the following primers: 5'KpnTUB5prom and 3'PstNOSterm. Run the following PCR reaction: 96° C. for 5 min followed by 20 cycles of 94° C. for 45 seconds, 60° C. for 30 seconds, 70° C. for 5 min, and 72° C. for 3 min.

Step 3. Transform plant, *Arabidopsis thaliana*

Step 3a. Sow *Arabidopsis* (L.) Heynh. ecotype Columbia (Col-0) seeds in 248 $cm^2$ plastic pots with moistened soil (Promix HP, Premier Horticulture Inc., Redhill, Pa., Canada). Grow plants at 20-21° C., with 60-70% relative humidity, under cool white fluorescent lights (140 umol $m^{-2}$ $s^{-1}$) with a 16 h light/8 h dark cycle. Water plants as needed by subrogation. After two weeks, transfer five individual plants to smaller pots (72 $cm^2$) for use in the transformation protocol. Grow the plants until the first floral buds and flowers form (2-3 additional weeks).

Step 3b. Grow an *Agrobacterium* colony for the construct to be transformed, in 500 ml of Terrific Broth plus spectinomycin (100 μg/ml) or streptomycin (200 μg/ml) for 2-3 days at 29° C. Collect cells by centrifugation at 6000 rpm for 15 minutes, and resuspend cells in 5% sucrose plus 0.05% surfactant (Silwet L-77, Lehle Seeds, Round Rock, Tex., USA) solution.

Step 3c. Transform plants by the floral dip transformation (13). Keep the plants in sealed containers to maintain high humidity for 16 to 24 h and maintain plants as described in step 3a. At 8 to 10 weeks dry plants, collect seeds and select for the marker. Select for the marker hygromycin resistance by incubating seeds on plates containing 4.418 g/L Murashige and Skoog Salt and Vitamin Mixture (MS medium, Life Technologies, Grand Island, N.Y., USA) plus hygromycin (50 μg/ml) and 0.8% (wt/vol) Phytagar. Collect and transfer positively selected plants into pots containing soil and grow for 5 to 6 weeks. Allow the plants to self-pollinate, collect seeds and repeat the selection process until homozygotes are identified.

EXAMPLE 2

Development of a Transgenic Plant that Non-Constitutively Expresses (Using an AtGLR1.1 Promoter) an Anchored Metabolic Regulator Containing a Putrescine Periplasmic Binding Protein Step 1. Prepare gene construct Make a gene construct that contains an AtGLR1.1 (locus tag At3 g04110) promoter with a putrescine periplasmic binding protein (putPBP) fused to a transmembrane and a NOS terminator in the following manner:

Step 1a. Use PCR to amplify the AtGLR1.1 promoter (−1438 to −1 bps) using 500 ng of DNA from an *Arabidopsis thaliana* Col-0 lambda genomic library. Add 500 ng of the following primers: 5'EcoRIAtGLR1.1prom (5'-TttttGAAT-TCtcatacatattcatacttgatg-3'; SEQ ID NO:9) and 3' SacAtGLR1.1prom (5'-ttttGAGCTCataatttchgtatagctctgt-3'; SEQ ID NO:10). (Note: the underlined nucleotides are restriction enzyme sites introduced into the primer during its synthesis.) Run the following PCR reaction: 96° C. for 5 min followed by 25 cycles of 94° C. for 45 seconds, 60° C. for 30 seconds, 70° C. for 3 min, and 72° C. for 3 min. Digest the resulting DNA fragment with SacI. Inactive the restriction enzyme.

Step 1b. Use PCR to amplify the putPBP gene and digest the resulting DNA fragment with SacI and KpnI as described in Example 1: step 1b.

Step 1c. Use PCR to amplify the transmembrane domain and digest the resulting DNA fragment with KpnI and XbaI as described in Example 1: step 1c.

Step 1d. Use PCR to amplify the NOS terminator, digest the resulting DNA fragment with XbaI, and inactivate the restriction enzyme as described in Example 1: step 1d.

Step 1e. Combine the digested fragments (from steps 1a, 1b, 1c, and 1d) and ligate at 4° C. overnight. Use the ligated fragment as a template for PCR to amplify the entire construct by adding 500 ng of the following primers: 5'EcoR1AtGLR1.1prom and 3'PstNOSterm. Run the following PCR reaction: 96° C. for 5 min followed by 20 cycles of 94° C. for 45 seconds, 60° C. for 30 seconds, 70° C. for 5 min, and 72° C. for 3 min. Digest the resulting DNA fragment with EcoRI and PstI and ligate into the vector pCAMBIA1105.1 that has been predigested with EcoRI and PstI.

Transform *E. coli*, select for antibiotic resistance, conduct PCR identification of cloned DNA constructs in transformants, purify DNA, and sequence (described in Example 1: step 1f).

Transform *Agrobacterium tumefaciens*: Transform the DNA construct into *Agrobacterium tumefaciens*, select for antibiotic resistance and confirm the presence of the DNA construct (described in Example 1: step 2).

Transform plant, *Arabidopsis thaliana*: Transform the DNA construct into *Arabidopsis thaliana*, select for antibiotic resistance, select for homozygote plants, and confirm the presence of the DNA construct (described in Example 1: step 3).

EXAMPLE 3

Development of a Transgenic Plant that Constitutively Expresses an Anchored Multiple Metabolic Regulator Containing a Putrescine and a Glutamate/Aspartate Periplasmic Binding Protein Make a gene construct that contains an AtTUB5 promoter with a putrescine periplasmic binding protein (putPBP) fused to a transmembrane fused to a glutamate/aspartate periplasmic binding protein (glu-aspPBP) and a NOS terminator in the following manner:

Step 1a. Use PCR to amplify the TUB5 promoter, digest the resulting DNA fragment with SacI, and inactivate the restriction enzyme (described in Example 1: step 1a).

Step 1b. Use PCR to amplify the putPBP gene, digest the resulting DNA fragment with SacI and KpnI, and inactivate the restriction enzyme (described in Example 1: step 1b).

Step 1c. Use PCR to amplify a transmembrane domain using 500 ng of DNA from a *Synechocystis* sp. strain PCC 6803 genomic library. Add 500 ng of the following primers: 5'KpnGLR0TM (5'-ttttGGTACCttttttggcatagccgctttgt-3'; SEQ ID NO:5) and 3'BamGLR0TM (5'-ttttGGATCCtaac-caaattaaattccccacc-3'; SEQ ID NO:11). Run the following PCR reaction: 96° C. for 5 min followed by 25 cycles of 94° C. for 45 seconds, 60° C. for 30 seconds, 70° C. for 1 min, and 72° C. for 3 min. Digest the resulting DNA fragment with KpnI and BamHI. Inactivate the restriction enzyme as described by manufacturer.

Step 1d. Use PCR to amplify the glu-aspPBP using 500 ng of DNA from *E. coli*. Add 500 ng of the following primers: 5'Bamglu-aspPBP (5'-ttttGGATCCatgtacgagtttgactggagtt-3'; SEQ ID NO:12) and 3'Xbaglu-aspPBP (5'-ttttTCTAGAt-tatgctgtccttcttttcaag-3'; SEQ ID NO:13). Run the following PCR reaction: 96° C. for 5 min followed by 25 cycles of 94° C. for 45 seconds, 60° C. for 30 seconds, 70° C. for 3 min, and 72° C. for 3 min. Digest the resulting DNA fragment with SacI and KpnI. Inactivate the restriction enzyme as described by the manufacturer.

Step 1e. Use PCR to amplify the NOS terminator, digest the resulting DNA fragment with XbaI, and inactivate the restriction enzyme (described in Example 1: step 1d).

Combine the digested fragments (from steps 1a, 1b, 1c, 1d and 1e) and ligate at 4° C. overnight. Use the ligated fragment as a template for PCR to amplify the entire construct by adding 500 ng of the following primers: 5'EcoR1TUB5prom and 3'PstNOSterm. Run the following PCR reaction: 96° C. for 5 min followed by 20 cycles of 94° C. for 45 seconds, 60° C. for 30 seconds, 70° C. for 5 min, and 72° C. for 3 min. Digest the resulting DNA fragment with EcoRI and PstI and ligate into the vector pCAMBIA1105.1 that has been predigested with EcoRI and PstI.

Transform *E. coli*, select for antibiotic resistance, conduct PCR identification of cloned DNA constructs in transformants, purify DNA and sequence (described in Example 1: step 1f).

Transform *Agrobacterium tumefaciens*: Transform the gene construct into *Agrobacterium tumefaciens*, select for antibiotic resistance, and confirm the presence of the DNA construct (described in Example 1: step 2).

Transform plant, *Arabidopsis thaliana*: Transform the gene construct into *Arabidopsis thaliana*, select for antibiotic resistance, select for homozygote plants, and confirm the presence of the DNA construct (described in Example 1: step 3).

EXAMPLE 4

Development of a Transgenic Plant that Constitutively Expresses a Soluble Multiple Metabolic Regulator Containing a Putrescine and a Glutamate/Aspartate Periplasmic Binding Protein Make a DNA construct that contains an AtTUB5 promoter with a putrescine periplasmic binding protein (putPBP) fused to a transmembrane fused to a glutamate/aspartate periplasmic binding protein (glu-aspPBP) and a NOS terminator in the following manner:

Step 1a. Use PCR to amplify the TUB5 promoter, digest the resulting DNA fragment with SacI, and inactivate the restriction enzyme (described in Example 1: step 1a).

Step 1b. Use PCR to amplify the putPBP gene, digest the resulting DNA fragment with SacI and KpnI, and inactivate the restriction enzyme (described in Example 1: step 1b).

Step 1c. Use PCR to amplify the glu-aspPBP using 500 ng of DNA from *E. coli* strain K12. Add 500 ng of the following primers: 5'Kpnglu-aspPBP (5'-ttttGGTACCatgtacgagtttga ctggagtt-3'; SEQ ID NO:14) and 3'Xbaglu-aspPBP (5'-ttttTCTAGAttatgctgtccttatttcaag-3'; SEQ ID NO:13). Run the following PCR reaction: 96° C. for 5 min followed by 25 cycles of 94° C. for 45 seconds, 60° C. for 30 seconds, 70° C. for 3 min, and 72° C. for 3 min. Digest the resulting DNA fragment with SacI and KpnI. Inactivate the restriction enzyme as described by the manufacturer.

Step 1d. Use PCR to amplify the NOS terminator, digest the resulting DNA fragment with XbaI, and inactivate the restriction enzyme (described in Example 1: step1D).

Combine the digested fragments (from steps 1a, 1b, 1c, and 1d) and ligate at 4° C. overnight. Use the ligated fragment as a template for PCR to amplify the entire fragment by adding 500 ng of the following primers: 5'EcoR1TUB5prom and 3'PstNOSterm. Run the following PCR reaction: 96° C. for 5 min followed by 20 cycles of 94° C. for 45 seconds, 60° C. for 30 seconds, 70° C. for 5 min, and 72° C. for 3 min. Digest the resulting DNA fragment with EcoRI and PstI and ligate into the vector pCAMBIA1105.1 that has been predigested with EcoRI and PstI.

Transform *E. coli*, select for antibiotic resistance, conduct PCR identification of cloned DNA constructs in transformants, purify DNA and sequence (described in Example 1: step 1f).

Transform *Agrobacterium tumefaciens*: Transform the DNA construct into *Agrobacterium tumefaciens*, select for antibiotic resistance, and confirm the presence of the DNA construct (described in Example 1: step 2).

Transform plant, *Arabidopsis thaliana*: Transform the DNA construct into *Arabidopsis thaliana*, select for antibiotic resistance, select for homozygote plants, and confirm the presence of the DNA construct (described in Example 1: step 3).

EXAMPLE 5

Development of a Transgenic Plant that Constitutively Expresses a Soluble Multiple Metabolic Regulator Containing a GABA$_B$R1b-LIVBP-LD and a Periplasmic C4-dicarboxylate Binding Protein Make a DNA construct that contains an AtTUB5 promoter with a GABA$_B$R1b-LIVBP-LD (GABA-LIVBP) fused to a transmembrane fused to a periplasmic C4-dicarboxylate binding protein (DctPBP) and a NOS terminator in the following manner:

Step 1a. Use PCR to amplify the AtTUB5 promoter (−1851 to −1 bps) using 500 ng of DNA from an *Arabidopsis thaliana* Col-0 lambda genomic library. Add 500 ng of the following primers: 5'KpnTUB5prom (5'-ttttGGTACCcacatttgcaaaatgatgaatg-3'; SEQ ID NO:15) and 3'PstTUB5prom (5'-ttttCTGCAGccaatctggttaccgcattgac-3'; SEQ ID NO:16). Run the following PCR reaction: 96° C. for 5 min followed by 25 cycles of 94° C. for 45 seconds, 60° C. for 30 seconds, 70° C. for 3 min, and 72° C. for 3 min. Digest the resulting DNA fragment with PstI. Inactivate the restriction enzyme as described by the manufacturer.

Step 1b. Use PCR to amplify the GABA-LIVBP using 500 ng of DNA from a cDNA library made from RNA isolated from mouse or rat brains. Add 500 ng of the following primers: 5'PstGABA-LIVBP (5'-ttttCTGCAGatgggcccgggggggaccctgta-3'; SEQ ID NO:17) and 3'NheGABA-LIVBP (5'-ttttGCTAGCctgagacaggaaacggaatgtc-3'; SEQ ID NO:18). Run the following PCR reaction: 96° C. for 5 min followed by 25 cycles of 94° C. for 45 seconds, 60° C. for 30 seconds, 70° C. for 3 min, and 72° C. for 3 min. Digest the resulting DNA fragment with PstI and NheI. Inactivate the restriction enzyme as described by the manufacturer.

Step 1c. Use PCR to amplify the DctPBP using 500 ng of DNA from *Rhodobacter capsulatus*. Add 500 ng of the following primers: 5'NhedctPBP (5'-ttttGCTAGCatgttgacccgtcg tatccttg-3'; SEQ ID NO:19) and 3'BamdctPBP (5'-ttttGGATCCttattccgccgtcgcggccttg-3'; SEQ ID NO:20). Run the following PCR reaction: 96° C. for 5 min followed by 25 cycles of 94° C. for 45 seconds, 60° C. for 30 seconds, 70° C. for 3 min, and 72° C. for 3 min. Digest the resulting DNA fragment with NheI and BamHI. Inactivate the restriction enzyme as described by the manufacturer.

Step 1d. Use PCR to amplify the NOS terminator using 500 ng of pPV1. Add 500 ng of the following primers 5'BamNOSterm (5'-ttttGGATCCtaccgagctcgaatttccccga-3'; SEQ ID NO:21) and 3'XbaNOSterm (5'-ttttTCTAGAgatctagtaacatagatgacac-3'; SEQ ID NO:22). Run the following PCR reaction: 96° C. for 5 min followed by 25 cycles of 94° C. for 45 seconds, 60° C. for 30 seconds, 70° C. for 3 min, and 72° C. for 3 min. Digest the resulting DNA fragment with BamHI. Inactivate the restriction enzyme as described by the manufacturer.

Combine the digested fragments (from steps 1a, 1b, 1c, and 1d) and ligate at 4° C. overnight. Use the ligated fragment as a template for PCR to amplify the entire fragment by adding 500 ng of the following primers: 5'Kpn1TUB5prom and 3'XbaNOSterm. Run the following PCR reaction: 96° C. for 5 min followed by 20 cycles of 94° C. for 45 seconds, 60° C. for 30 seconds, 70° C. for 5 min, and 72° C. for 3 min. Digest the resulting DNA fragment with KpnI and XbaI and ligate into the vector pCAMBIA1105.1 that has been predigested with KpnI and XbaI.

Transform *E. coli*, select for antibiotic resistance, conduct PCR identification of cloned DNA constructs in transformants, purify DNA and sequence (described in Example 1: step 1f).

Transform *Agrobacterium tumefaciens*: Transform the DNA construct into *Agrobacterium tumefaciens*, select for antibiotic resistance, and confirm the presence of the DNA construct (described in Example 1: step 2).

Transform plant, *Arabidopsis thaliana*: Transform the DNA construct into *Arabidopsis thaliana*, select for antibiotic resistance, select for homozygote plants, and confirm the presence of the DNA construct (described in Example 1: step 3).

EXAMPLE 6

Development of a Transgenic Plant that Expresses a Soluble Metabolic Regulator Containing a Glutamate/Aspartate Periplasmic Binding Protein in the Plastids of Seeds Using Fusion PCR Make a DNA construct that contains an seed specific promoter (locus tag At5 g38170 from *Arabidopsis*) with an in-frame plastid transit peptide for the pyruvate kinase beta subunit fused to a glutamate/aspartate periplasmic binding protein and myc-c tag with a NOS terminator in the following manner:

Step 1a. Use PCR to amplify the seed specific promoter (−1805 to −1 bps) with a short overlap of the 5' end of the plastid transit peptide at the 3' end of the promoter using 500 ng of genomic DNA isolated from an *Arabidopsis thaliana* Col-0. Add 300 nM of the following primers: MG1P1 (5'-tctttatgtaacaatgagtcgatgg-3'; SEQ ID NO:23) and MG1P3 (5'-gatttgaccataagcagccatgtcttcaaactctaggaacttttc-3'; SEQ ID NO:24). Run the PCR as described in (202).

Step 1b. Use PCR to amplify the plastid transit peptide for the pyruvate kinase beta subunit using 500 ng of genomic DNA isolated from an *Arabidopsis thaliana* Col-0. Add 300 nM the following primers: 5' oTP (5'-atggctgcttatggtcaaatc-3'; SEQ ID NO:25) and 3' oTP (5'-gat tttaatcgatctaacggag-3'; SEQ ID NO:26). Run the PCR as described in (202).

Step 1c. Use PCR to amplify a glutamate/aspartate periplasmic binding protein fused in-frame with a myc-c tag (3'-end) with a short overlap of the 3'-end of the transit peptide for the pyruvate kinase beta subunit on the 5' and a short overlap of the 5'-end of the NOS terminator on the 3'-end, using 500 ng of DNA from *E. coli* strain K12. Add 300 nM the following primers: MG1P4 (5'-ctccgttagatcgattaaaatcgcaggcagcacgctggac-3'; SEQ ID NO:27) and pMG1P5 (5'-gga aattcgagctcggtagcctacagatcttcttcagaaataag-3'; SEQ ID NO:28). Run the PCR as described in (202).

Step 1d. Use PCR to amplify the NOS terminator using 500 ng of pPV1. Add 300 nM of the following primers 5' pNOS (5'-gctaccgagctcgaatttcc-3'; SEQ ID NO:29) and MG1P7 (5'-tta agttgggtaacgccagg-3'; SEQ ID NO:30). Run the PCR as described Szewczyk et al., 2006.

Step 1e. Combine the amplified fragments from steps 1a, 1b, 1c, and 1d and 300 nM of the following primers MG1P2 (5'-ttttGGTACCaagatggagggcagtaggtg-3'; SEQ ID NO:31) and MG1P6 (5'-ttttAAGCTTcccgatctagtaacatagatg-3'; SEQ ID NO:32). Run the PCR as described Szewczyk et al., 2006. Clone into pCR4.0-TOPO as described by the manufacturer (Invitrogen).

Step 1f. Transform *E. coli*, select for antibiotic resistance, conduct PCR identification of cloned DNA constructs in transformants, purify DNA and sequence (described in Example 1: step 1f). Digest the plasmid with Acc65I and HindIII, isolate DNA fragment and ligate into the vector pCAMBIA1300 that has been predigested with Acc65I and HindIII.

Transform *Agrobacterium tumefaciens*: Transform the DNA construct into *Agrobacterium tumefaciens*, select for antibiotic resistance, and confirm the presence of the DNA construct (described in Example 1: step 2).

Transform plant, *Arabidopsis thaliana*: Transform the DNA construct into *Arabidopsis thaliana*, select for antibiotic resistance, select for homozygote plants, and confirm the presence of the DNA construct (described in Example 1: step 3).

EXAMPLE 7

Development of a Transgenic Plant that Expresses a Soluble Metabolic Regulator Containing Two Fused Glutamate/Aspartate Periplasmic Binding Proteins in the Plastids of Seeds Using Fusion PCR (Double Metabolic Regulator)

Make a DNA construct that contains a seed specific promoter (locus tag At5 g38170 from *Arabidopsis*) with an in-frame plastid transit peptide for the pyruvate kinase beta subunit fused to a glutamate/aspartate periplasmic binding protein with a linker followed by second glutamate/aspartate periplasmic binding protein with a myc-c tag with a NOS terminator in the following manner:

Step 1a. Use PCR to amplify the first portion (seed specific promoter, plastid transit peptide pyruvate kinase beta subunit, first glutamate/aspartate periplasmic binding protein and linker) of the double metabolic regulator using 100 ng of plasmid DNA containing the single a glutamate/aspartate periplasmic binding protein (described in Example 6: step 1e and 1f.). Add 300 nM of the following primers: T7 (5'-taatacgactcactataggg-3'; SEQ ID NO:33) and MG2P3 (5'-cttatccgcgttaacttcgccttcagtactgttcagtgccttgtcattcgg-3'; SEQ ID NO:34). Run the PCR as described in (202).

Step 1b. Use PCR to amplify the second portion (linker, the second glutamate/aspartate periplasmic binding protein, myc-c tag and NOS terminator) of the double metabolic regulator using 100 ng of plasmid DNA containing the single a glutamate/aspartate periplasmic binding protein (described in Example 6: step 1e and 1f.). Add 300 nM of the following primers: T3 (5'-attaaccctcactaaaggga-3'; SEQ ID NO:35) and MG2P4 (5'-cgaa gttaacgcggaagaagaaggctttgcaggcagcacgctggac-3'; SEQ ID NO:36). Run the PCR exactly as described in (202).

Combine the amplified fragments from steps 1a, and 1b and 300 nM of the following primers MG1P2 (5'-ttttGGTACCaagatggagggcagtaggtg-3'; SEQ ID NO:31) and MG1P6 (5'-ttttAAGCTTcccgatctagtaacatagatg-3'; SEQ ID NO:32). Run the PCR as described Szewczyk et al., 2006. Clone into pCR4.0-TOPO as described by the manufacturer (Invitrogen).

Transform *E. coli*, select for antibiotic resistance, conduct PCR identification of cloned DNA constructs in transformants, purify DNA and sequence (described in Example 1: step 10. Digest the plasmid with Acc65I and HindIII, isolate DNA fragment and ligate into the vector pCAMBIA1300 that has been predigested with Acc65I and HindIII.

Transform *Agrobacterium tumefaciens*: Transform the DNA construct into *Agrobacterium tumefaciens*, select for antibiotic resistance, and confirm the presence of the DNA construct (described in Example 1: step 2).

Transform plant, *Arabidopsis thaliana*: Transform the DNA construct into *Arabidopsis thaliana*, select for antibiotic resistance, select for homozygote plants, and confirm the presence of the DNA construct (described in Example 1: step 3).

EXAMPLE 8

Development of a Transgenic Plant that Expresses a Soluble Metabolic Regulator Containing a Glutamate/Aspartate Periplasmic Binding Protein in the Vascular Tissue of Seeds Using Fusion PCR Make a DNA construct that contains an glutamate receptor 1.1 promoter (locus tag At3 g04110 from *Arabidopsis*) with an in-frame transit peptide (locus tag At3 g20570 from *Arabidopsis*) for fused to a glutamate/aspartate periplasmic binding protein and myc-c tag with a NOS terminator in the following manner:

Step 1a. Use PCR to amplify the glutamate receptor 1.1 promoter (−1400 to −1 bps) with a short overlap the 5'-end of the transit peptide at the 3'-end of the promoter using 500 ng of genomic DNA isolated from an *Arabidopsis thaliana* Col-0. Add 300 nM of the following primers: 1.1MG1P1 (5'-gatcatacatattcatacttgatg-3'; SEQ ID NO:37) and 1.1stMG1P3 (5'-ctctttag gtttcgtgccatataatttcttgtatagctctgtaac-3'; SEQ ID NO:38). Run the PCR as described Szewczyk et al., 2006.

Step 1b. Use PCR to amplify the transit peptide for Locus ID # At3 g20570 using 500 ng of genomic DNA isolated from an *Arabidopsis thaliana* Col-0. Add 300 nM the following primers: 5' stTP (5'-atggcacgaaacctaaagag-3'; SEQ ID NO:39) and 3' stTP (5'-agcgtaggctcggtca acg-3'; SEQ ID NO:40). Run the PCR as described in (202).

Step 1c. Use PCR to amplify a glutamate/aspartate periplasmic binding protein fused in-frame with a myc-c tag with a short overlap of the 3'-end of Locus ID # At3 g20570 at the 5' end and short overlap of the 5'-end of NOS terminator at the 3'-end of the glutamate/aspartate periplasmic binding protein, using 500 ng of DNA from *E. coli* strain K12. Add 300 nM the following primers: 1.1stMG1P4 (5'-cgttgaccgagcctacgctg-caggcagcacgctggac-3'; SEQ ID NO:41) and pMG1P5 (5'-ggaaattcgagctcggtagcctacagatcttcttcagaaataag-3'; SEQ ID NO:42). Run the PCR as described Szewczyk et al., 2006.

Step 1d. Use the NOS terminator that was amplified in Example 6: Step 1d.

Step 1e. Combine the amplified fragments from steps 1a, 1b, 1c, and 1d and 300 nM of the following primers 1.1MG1P2 (5'-ttttGGTACCcgaagetcaatcgtetcgag-3'; SEQ ID NO:43) and MG1P6 (5'-ttttAAGCTTcccgatctagtaacata-gatg-3'; SEQ ID NO:32). Run the PCR as described Szewczyk et al., 2006. Clone into pCR4.0-TOPO as described by the manufacturer (Invitrogen).

Step 1£ Transform *E. coli*, select for antibiotic resistance, conduct PCR identification of cloned DNA constructs in transformants, purify DNA and sequence (described in Example 1: step 10. Digest the plasmid with Acc65I and HindIII, isolate DNA fragment and ligate into the vector pCAMBIA1300 that has been predigested with Acc65I and HindIII.

Transform *Agrobacterium tumefaciens*: Transform the DNA construct into *Agrobacterium tumefaciens*, select for antibiotic resistance, and confirm the presence of the DNA construct (described in Example 1: step 2).

Transform plant, *Arabidopsis thaliana*: Transform the DNA construct into *Arabidopsis thaliana*, select for antibiotic resistance, select for homozygote plants, and confirm the presence of the DNA construct (described in Example 1: step 3).

EXAMPLE 9

Development of a Transgenic Plant that Expresses a Cytosolic Soluble Metabolic Regulator, Using Chemical Synthesis Step 1: Use chemical synthesis to make a DNA construct that contains a tissue-specific promoter SEQ ID NO: 44, 45, 46 or 47 fused with a SEQ ID NO: 48 and a NOS terminator. Clone the DNA construct into a binary vector such as pCambia1300, pCambia2300 or pCambia3200. The sequences are as follows.

SEQ ID NO:44 is a seed-specific pyruvate kinase promoter from *Arabidopsis thaliana;*

SEQ ID NO:45 is a seed-specific napin promoter from canola (*Brassica napus* L.);

SEQ ID NO:46 is a seed-specific alpha' beta-conglycinin subunit promoter from soybean (*Glycine max*);

SEQ ID NO:47 is a seed-specific phaseolin promoter from common bean (*Phaseolus vulgaris* L.); and SEQ ID NO:48 encodes a peptide for a truncated GluAsp periplasmic binding protein from *E. coli* optimized for expression in canola (*B. napus* L.), a dicot.

Step 2: Transform *Agrobacterium tumefaciens*: Transform the DNA construct into *Agrobacterium tumefaciens*, select for resistance and confirm the presence of the DNA construct.

Step 3: Transform plant, *Arabidopsis*, soybean, corn, cotton, camelina, canola, sunflower, or safflower, select for antibiotic resistance, select for transgenic plants. Confirm the presence of the DNA constructs.

EXAMPLE 10

Development of a Transgenic Plant that Expresses an Organelle-Targeted Metabolic Regulator Using Chemical Synthesis Step 1: Use chemical synthesis to make a DNA construct that contains a tissue-specific promoter SEQ ID NO: 44, 45, 46 or 47 fused with a SEQ ID NO:49 and a NOS terminator. Clone the DNA construct into a binary vector such as pCambia1300, pCambia2300 or pCambia3200. SEQ ID NO:49 encodes a plastid transit peptide from *Arabidopsis* fused to a truncated GluAsp periplasmic binding protein from *E. coli* optimized for expression in canola (*B. napus* L.), a dicot.

Step 2: Transform *Agrobacterium tumefaciens*: Transform the DNA construct into *Agrobacterium tumefaciens*, select for resistance and confirm the presence of the DNA construct.

Step 3: Transform plant, *Arabidopsis*, soybean, corn, cotton, camelina, canola, sunflower, or safflower, select for herbicide resistance, select for transgenic plants. Confirm the presence of the DNA constructs.

EXAMPLE 11

Development of a Transgenic Plant that Expresses an Apoplastic-Targeted Metabolic Regulator Using Chemical Synthesis Step 1: Use chemical synthesis to make a DNA construct that contains a tissue-specific promoter (AtGLR1.1 promoter) fused with a SEQ ID NO: 50 or 51 and a NOS terminator. Clone the DNA construct into a binary vector such as pCambia1300, pCambia2300 or pCambia3200. The sequences are as follows:

SEQ ID NO:50 encodes an apoplastic transit peptide from *Arabidopsis* fused to a truncated GluAsp periplasmic binding protein from *E. coli* optimized for expression in canola (*B. napus* L.), a dicot; and SEQ ID NO:51 encodes an apoplastic transit peptide from *Arabidopsis* fused to a truncated polyamine periplasmic binding protein (PotD) from *E. coli* optimized for expression in *Arabidopsis*, a dicot.

Step 2: Transform *Agrobacterium tumefaciens*: Transform the DNA construct into *Agrobacterium tumefaciens*, select for resistance and confirm the presence of the DNA construct.

Step 3: Transform plant, *Arabidopsis*, soybean, corn, cotton, camelina, canola, sunflower, or safflower, select for antibiotic resistance, select for homozygote plants. Confirm the presence of the DNA constructs.

EXAMPLE 12

Use of a Soluble Metabolic Regulator Expressed in Seed to Improve Seed Quality in a Plant 12A. Transgenic plants with a soluble metabolic-regulator gene construct have increased seed weight In *Arabidopsis*, average seed weight is strongly correlated with total oil content (204). To demonstrate that the average seed weight in transgenic *Arabidopsis* plants with a soluble metabolic-regulator gene construct is greater than in control plants, *Arabidopsis* was transformed with a construct similar to that described in Example 9. As used herein, a similar construct means a construct that also had codon optimization and was further modified in the nucleotide sequence around the start codon to optimize expression in transgenic plants (205, 206). Control plants were *Arabidopsis* plants transformed with an empty vector, i.e., the vector without a foreign gene, and referred to as empty vector controls (EVC). Transformed plants were confirmed by selection and PCR analysis. Transgenic plants were grown in soil (Metro Mix 360) for 60 days. The growth conditions were maintained at 20-21° C., under cool white fluorescent lights (120 umol of photons per $m^2$ per s) with a 16-h light/8-h dark cycle. Plants were allowed to dry, and when dry, the seeds were collected and cleaned, and 200 seeds from each of the lines were weighed. The average seed weight in the EVC lines (n=12) was 20.0 ug (SD=3.0), and the average seed weight in the lines with the gene construct (n=25) was 23.9 ug (SD=4.1), p=0.002. Thus the transgenic plants with the soluble metabolic-regulator gene construct had 20% greater seed weight than the EVC plants.

12B. Transgenic plants with a soluble metabolic-regulator gene construct have increased seed oil Camelina was transformed with a construct similar to that described in Example 9, and independently transformed EVC were used as controls. Transformed plants were confirmed by selection and PCR analysis. The plants were grown in soil (Metro Mix 360) for 90 days. The growth conditions were maintained at 20-21° C., under cool white fluorescent lights (240 umol of photons per $m^2$ per s) with a 16-h light/8-h dark cycle. Plants were allowed to dry, and seeds were collected and cleaned. Total oil was extracted and determined using FAME analysis with a Tri-17:0 standard. The average total oil content of the seed from the camelina plants with the soluble cytosolic metabolic regulator was 35.1%, whereas the average total oil content of the seed from the EVC plants was 33.0%. The seed oil in the transgenic camelina plants with a soluble metabolic-regulator gene construct was 2.1% higher than in the EVC plants.

Canola was transformed with a construct similar to that described in Example 9, and independently transformed EVC were used as controls. Transformed plants were confirmed by selection and PCR analysis. Transgenic plants were grown in soil (Metro Mix 360) for 120 days. The growth conditions were maintained at 20-21° C., under cool white fluorescent lights (240 umol of photons per $m^2$ per s) with a 16-h light/8-h dark cycle. Plants were allowed to dry, and seeds were collected and cleaned. Total oil was extracted and determined using FAME analysis with a Tri-17:0 standard. The average total oil content of the seed from the canola plants with the soluble cytosolic metabolic regulator was 33.1%, whereas the average total oil content of the seed from the EVC plants was 29.8%. The seed oil in the transgenic canola plants with a soluble metabolic-regulator gene construct was 3.3% higher than in the EVC plants.

EXAMPLE 13

Use of an Organelle-Targeted Metabolic Regulator Expressed in Seed to Improve Seed Quality in a Plant 13A. Transgenic plants with an organelle-targeted metabolic-regulator gene construct expressed in developing seeds have increased seed weight

*Arabidopsis* was transformed with an organelle-targeted metabolic-regulator gene construct similar to that described in Example 10, and independently transformed EVC were used as controls. Transformed plants were confirmed by selection and PCR analysis. Transgenic plants were grown in soil (Metro Mix 360) for 60 days. The growth conditions were maintained at 20-21° C., under cool white fluorescent lights (120 umol of photons per $m^2$ per s) with a 16-h light/8-h dark cycle. Plants were allowed to dry, and when dry, the seeds were collected and cleaned, and 200 seeds from each of the lines were weighed. The average seed weight in the EVC lines (n=12) was 20.0 ug (SD=3.0), and the average seed weight in the lines with the gene construct (n=28) was 23.1 ug (SD=3.9), p=0.01. Thus the transgenic plants with an organelle-targeted metabolic-regulator gene construct had 16% greater seed weight than the EVC plants.

13B. Transgenic plants with an organelle-targeted metabolic-regulator gene construct expressed in developing seeds have a higher carbon-to-nitrogen ratio In *Arabidopsis* seeds, the carbon-to-nitrogen (C:N) ratio is highly correlated (r=0.89) with the percentage of oil (204). To assess the magnitude of carbon redistribution in the seed of *Arabidopsis* plants transformed with an organelle-targeted metabolic-regulator gene construct similar to that described in Example 10, the C:N ratio was analyzed. Transformed plants were confirmed by selection and PCR analysis. Transgenic plants and WT plants were grown in soil (Metro Mix 360) for 60 days. The growth conditions were maintained at 20-21° C., under cool white fluorescent lights (120 umol of photons per $m^2$ per s) with a 16-h light/8-h dark cycle. Three sets of mature seeds from three transgenic and three WT lines were shipped to the Duke Environmental Stable Isotope Laboratory for C and N analysis. The seeds (4 to 5 mg per sample) were combusted at 1200° C. in an elemental analyzer (CE Instruments NC 2100 Elemental Analyzer, ThermoQuest) in the presence of chemical catalysts to produce $CO_2$ and N.

Table 1 shows the average percentage of seed C and N and the C:N ratios for the WT and transgenic lines. The last column shows the relative C:N ratio of the transgenic lines to the WT line. As shown, the C:N ratio was higher in all the transgenic lines compared to WT. Planned comparison t-tests, performed on the mean C:N ratios of each transgenic line and WT line, indicated that the C:N ratios of the transgenic lines were significantly higher than the mean C:N ratio of the WT line (p<0.0001 for all transgenic lines).

TABLE 1

Percentages of seed Carbon and Nitrogen in transgenic and WT lines

| Line | % C Mean (SD) | % N Mean (SD) | C:N Mean (SD) | C:N relative to WT |
|---|---|---|---|---|
| WT | 52.2 (0.47) | 4.2 (0.19) | 12.4 (0.66) | |
| Line 1 | 56.7 (0.01) | 3.3 (0.034) | 17.2 (0.18) | 138% |
| Line 2 | 57.1 (0.20) | 3.1 (0.052) | 18.2 (0.35) | 146% |
| Line 3 | 56.7 (0.03) | 3.4 (0.012) | 16.9 (0.07) | 136% |

13C. Transgenic plants with an organelle-targeted metabolic-regulator gene construct have increased seed oil Canola was transformed with a construct similar to that described in Example 10, and independently transformed EVC were used as controls. Transformed plants were confirmed by selection and PCR analysis. Transgenic plants were grown in soil (Metro Mix 360) for 120 days. The growth conditions were maintained at 20-21° C., under cool white fluorescent lights (240 umol of photons per $m^2$ per s) with a 16-h light/8-h dark cycle. Plants were allowed to dry, and seeds were collected and cleaned. Total oil was extracted and determined using FAME analysis with a Tri-17:0 standard. The average total oil content of the seed from the canola plants with the organelle-targeted metabolic regulator was 31.3%, whereas the average total oil content of the seed from the EVC plants was 29.8%. The seed oil in the transgenic canola plants with the organelle-targeted metabolic-regulator gene construct was 1.5% higher than in the EVC plants.

EXAMPLE 14

Figure 3:
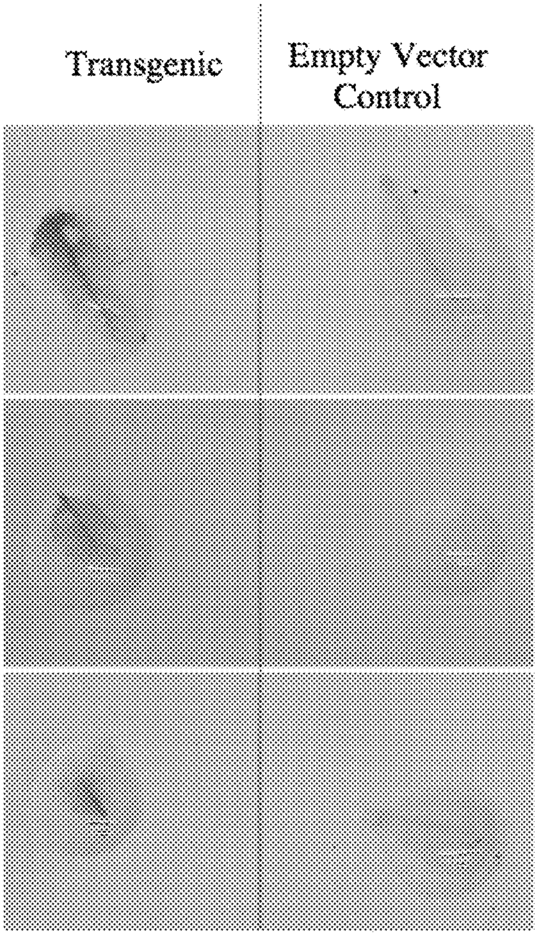
FIG. 3 shows lignin-stained leaves of three representative transgenic plants with the apoplastic-targeted metabolic regulator (left column) and three representative EVC plants (right column).

Use of an Apoplastic-Targeted Metabolic Regulator to Improve Crop Quality, such as Increased Lignin Content This example demonstrates the use of an apoplastic-targeted metabolic regulator to improve crop quality, such as increased lignin content. *Arabidopsis* was transformed with a construct similar to that described in Example 11. EVC served as controls. Transformed plants were confirmed by selection and PCR analysis. Transgenic plants were grown in soil (Metro Mix 360) for 60 days. The growth conditions were maintained at 20-21° C., under cool white fluorescent lights (120 umol of photons per $m^2$ per s) with a 16-h light/8-h dark cycle. After day 21, leaves were removed from the plants and stained for lignin using a combination of saturated phloroglucinol, 95% ethanol, and 18% HCl. FIG. 3 shows lignin-stained leaves of three representative transgenic plants with the apoplastic-targeted metabolic regulator (left column) and three representative EVC plants (right column). The representative leaves were photographed and the amount of staining was quantified using densitometry. The transgenic plants with the apoplastic-targeted metabolic regulator had, on average, 21% more staining than the EVC plants.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

BIBLIOGRAPHY

1. Acher & Bertrand 2005, "Amino acid recognition by Venus flytrap domains is encoded in an 8-residue motif" Biopolymers, 80: 357-366.
2. Adler et al. 2005, U.S. Pat. No. 6,955,887.
3. Altschul et al., 1997, "Gapped BLAST and PSI-BLAST: a new generation of protein database search programs." Nucleic Acids Res, 25: 3389-3402.
4. Amiss et al., 2005. United States Patent Application 20050112685.
5. Amoah et al., 2001, "Factors influencing *Agrobacterium*-mediated transient expression of uidA in wheat inflorescence tissue." J Exp Bot, 52: 1135-1142.
6. An et al., 1985, "New cloning vehicles for transformation of higher plants." EMBO. J., 4: 277-284.
7. Armstrong et al., 1998, "Structure of a glutamate-receptor ligand-binding core in complex with kainate." Nature, 395: 913-917.
8. Ausubel et al., 1995, "Current protocols in molecular biology." New York: Greene Publishing and Wiley-Interscience.
9. Avsian-Kretchmer et al., 2004, "The salt-stress signal transduction pathway that activates the gpx1 promoter is mediated by intracellular H2O2, different from the pathway induced by extracellular H2O2." Plant Physiol, 135: 1685-1696.
10. Badr et al., 2005, "Production of fertile transgenic wheat plants by laser micropuncture." Photochem. Photobiol. Sci., 4: 803-807.
11. Bannai et al., 2002, "Extensive feature detection of N-terminal protein sorting signals." Bioinformatics, 18: 298-305.
12. Bao et al., 1997, "Transfection of a reporter plasmid into cultured cells by sonoporation in vitro." Ultrasound in Medicine and Biology, 23: 953-959.
13. Bechtold & Pelletier, 1998, "In planta *Agrobacterium*-mediated transformation of adult *Arabidopsis thaliana* plants by vacuum infiltration." Methods Mol Biol, 82: 259-266.
14. Bendtsen et al., 2004, "Improved prediction of signal peptides: SignalP 3.0." J Mol Biol, 340: 783-795.
15. Bevan & Chilton, 1982, "T-DNA of the *Agrobacterium* Ti and Ri plasmids." Ann. Rev. Genet., 16: 357-384.
16. Bhasin et al., 2005, "PSLpred: prediction of subcellular localization of bacterial proteins." Bioinformatics, 21: 2522-2524.
17. Bhasin & Raghava, 2004, "ESLpred: SVM-based method for subcellular localization of eukaryotic proteins using dipeptide composition and PSI-BLAST." Nucleic Acids Res, 32: W414-419.
18. Chan & Wells, 1974, "Structural uniqueness of lactose operator." Nature, 252: 205-209.
19. Chen et al., 1996, "The promoter of a H2O2-inducible, *Arabidopsis* glutathione S-transferase gene contains closely linked OBF- and OBP1-binding sites." Plant J, 10: 955-966.
20. Chen et al., 1999, "Functional characterization of a potassium-selective prokaryotic glutamate receptor." Nature, 402: 817-821.
21. Chen et al., 2006. U.S. Pat. No. 7,083,945.
22. Chen et al., 2002, "Transmembrane helix predictions revisited." Protein Sci, 11: 2774-2791.
23. Chen & Singh, 1999, "The auxin, hydrogen peroxide and salicylic acid induced expression of the *Arabidopsis* GST6 promoter is mediated in part by an ocs element." Plant J, 19: 667-677.
24. Chiu et al., 2002, "Phylogenetic and expression analysis of the glutamate-receptor-like gene family in *Arabidopsis thaliana*." Mol Biol Evol, 19: 1066-1082.
25. Chiu et al., 1999, "Molecular evolution of glutamate receptors: a primitive signaling mechanism that existed before plants and animals diverged." Mol Biol Evol, 16: 826-838.
26. Christou et al., 1987, "Stable transformation of soybean by electroporation and root formation from transformed callus." Proc Natl Acad Sci USA, 84: 3962-3966.
27. Claros & Vincens, 1996, "Computational method to predict mitochondrially imported proteins and their targeting sequences." Eur J Biochem, 241: 779-786.
28. Claverie & States, 1993, "Information enhancement methods for large scale sequence analysis." Comput. Chem., 17: 191-201.
29. Cokol et al., 2000, "Finding nuclear localization signals." EMBO Rep, 1: 411-415.
30. Cormack et al., 2002, "Leucine zipper-containing WRKY proteins widen the spectrum of immediate early elicitor-induced WRKY transcription factors in parsley." Biochim Biophys Acta, 1576: 92-100.
31. Coruzzi & Bush, 2001, "Nitrogen and carbon nutrient and metabolite signaling in plants." Plant Physiol, 125: 61-64.
32. Coruzzi et al., 2001. U.S. Pat. No. 6,177,275.
33. Coruzzi et al., 2004. U.S. Pat. No. 6,822,079.
34. Coruzzi et al., 1998. U.S. Pat. No. 5,824,867.
35. Coruzzi et al., 1999a. U.S. Pat. No. 5,959,174.
36. Coruzzi et al., 1999b. U.S. Pat. No. 5,981,703.
37. Coruzzi et al., 2002. U.S. Pat. No. 6,451,546.
38. Coruzzi & Zhou, 2001, "Carbon and nitrogen sensing and signaling in plants: emerging 'matrix effects'." Curr Opin Plant Biol, 4: 247-253.
39. Crossway et al., 1986, "Integration of foreign DNA following microinjection of tobacco mesophyllprotoplasts." Mol. Gen. Genet., 202: 179-185.
40. Cserzo et al., 2002, "On filtering false positive transmembrane protein predictions." Protein Eng, 15: 745-752.
41. Cserzo et al., 1997, "Prediction of transmembrane alpha-helices in prokaryotic membrane proteins: the dense alignment surface method." Prot. Eng. vol. 10, no. 6, 1997, 10: 673-676.
42. D'Halluin et al., 1992, "Transgenic. maize plants by tissue electroporation." Plant Cell 4: 1495-1505, 4: 1495-1505.
43. Davenport 2002, "Glutamate receptors in plants." Annals of Botany, 90: 549-557.
44. de Framond 1991, "A metallothionein-like gene from maize (*Zea mays*). Cloning and characterization." FEBS Lett, 290: 103-106.
45. Dennison & Spalding, 2000, "Glutamate-gated calcium fluxes in *Arabidopsis*." Plant Physiology, 124: 1511-1514.
46. Deshayes et al., 1985, "Liposome-mediated transformation of tobacco mesophyllprotoplasts by an *Escherichia coli* plasmid." Embo J, 4: 2731-2737.
47. Dhringra & Sinclair, 1985, "Basic plant pathology methods." Boca Raton, Fla.: CRC Press.
48. Dubos et al., 2003, "A role for glycine in the gating of plant NMDA-like receptors." Plant J, 35: 800-810.
49. Dubos et al., 2005, "Kanamycin reveals the role played by glutamate receptors in shaping plant resource allocation." Plant J, 43: 348-355.
50. Eastman et al., 2006, "Thematic review series: lipid post-translational modifications. Fighting parasitic disease by blocking protein farnesylation." J Lipid Res, 47: 233-240.
51. Emanuelsson et al., 2007, "Locating proteins in the cell using TargetP, SignalP and related tools." Nat Protoc, 2: 953-971.
52. Emanuelsson et al., 2000, "Predicting subcellular localization of proteins based on their N-terminal amino acid sequence." J Mol Biol, 300: 1005-1016.
53. Emanuelsson et al., 1999, "ChloroP, a neural network-based method for predicting chloroplast transit peptides and their cleavage sites." Protein Sci, 8: 978-984.
54. Eulgem et al., 1999, "Early nuclear events in plant defence signalling: rapid gene activation by WRKY transcription factors." Embo J, 18: 4689-4699.
55. Felder et al., 1999, "The Venus flytrap of periplasmic binding proteins: an ancient protein module present in multiple drug receptors." AAPS PharmSci, 1: E2.
56. Feng & Doolittle, 1987, "Progressive sequence alignment as a prerequisite to correct phylogenetic trees." J Mol Evol, 25: 351-360.
57. Fernando et al., 2004, "THGS: a web-based database of Transmembrane Helices in Genome Sequences." Nucleic Acids Res, 32: D125-128.
58. Ferrario-Mery et al., 2005, "Physiological characterisation of *Arabidopsis* mutants affected in the expression of the putative regulatory protein PII." Planta, 223: 28-39.
59. Finer & Finer, 2000, "Use of *Agrobacterium* expressing green fluorescent protein to evaluate colonization of sonication-assisted *Agrobacterium*-mediated transformation-treated soybean cotyledons." Lett Appl Microbiol, 30: 406-410.
60. Forde & Lea, 2007, "Glutamate in plants: metabolism, regulation, and signalling." J Exp Bot, 58: 2339-2358.
61. Frame et al., 1994, "Production of fertile transgenic maize plants by silicon carbide whisker-mediated transformation." Plant J., 6.
62. Freeman et al., 1984, "A Comparison of Methods for Plasmid Delivery into Plant Protoplasts." Plant and Cell Physiol, 25: 1353-1365.
63. Fromm et al., 1985, "Expression of genes transferred into monocot and dicot plant cells by electroporation." Proc Nat Aca Sci, 82: 5824-5828.
64. Fromm et al., 1986, "Stable transformation of maize after gene transfer by electroporation." Nature, 319: 791-793.
65. Gait, 1984, "Oligonucleotide Synthesis-A Practical Approach." Washington, D.C.: IRL Press.
66. Galvez et al., 1999, "Mutagenesis and modeling of the GABAB receptor extracellular domain support a Venus flytrap mechanism for ligand binding." J Biol Chem, 274: 13362-13369.
67. Garg et al., 2005, "Support vector machine-based method for subcellular localization of human proteins using amino acid compositions, their order, and similarity search." J Biol Chem, 280: 14427-14432.
68. Goeddel et al., 1980, "Synthesis of human fibroblast interferon by *E. coli*." Nucleic Acids Res, 8: 4057-4074.
69. Goff 2002, "Collaboration on the rice genome." Science, 296: 45.
70. Gould et al., 1989, "A conserved tripeptide sorts proteins to peroxisomes." J Cell Biol, 108: 1657-1664.
71. Gould et al., 1988, "Identification of peroxisomal targeting signals located at the carboxy terminus of four peroxisomal proteins." J Cell Biol, 107: 897-905.
72. Griesbach 1983, "Protoplast microinjection." Plant Mol. Biol. Rep., q: 32-37.
73. Gromiha et al., 2005, "TMBETA-NET: discrimination and prediction of membrane spanning beta-strands in outer membrane proteins." Nucleic Acids Res, 33: W164-167.
74. Gruber & Cosby. (1993). Vectors for plant transformation. In B. R. Glick & J. E. Thompson (Eds.), Methods in Plant Molecular Biology and Biotechnology (pp. 89-119). Baco Raton, Fla.: CRC Press.
75. Guo et al., 1995, "Laser-mediated gene transfer in rice." Physiol. Plant., 93: 19-24.
76. Hames & Higgins, 1984, "Nucleic acid hybridization, a practical approach." Washington D.C.: IRL Press.
77. Helenius & Aebi, 2001, "Intracellular functions of N-linked glycans." Science, 291: 2364-2369.
78. Henikoff & Henikoff, 1989, "Amino acid substitution matrices from protein blocks." Proc. Natl. Acad. Sci. USA, 89: 10915-10919.
79. Herrera-Estrella et al., 1983, "Expression of chimaeric genes transferred into plant cells using a Ti-plasmid-derived vector." Nature, 303: 209-213.
80. Higgins et al., 1992, "CLUSTAL V: improved software for multiple sequence alignment." Comput Appl Biosci, 8: 189-191.
81. Higgins & Sharp, 1988, "CLUSTAL: a package for performing multiple sequence alignment on a microcomputer." Gene, 73: 237-244.
82. Higgins & Sharp, 1989, "Fast and sensitive multiple sequence alignments on a microcomputer." Comput Appl Biosci, 5: 151-153.
83. Hiller et al., 2004, "PrediSi: prediction of signal peptides and their cleavage positions." Nucleic Acids Res, 32: W375-379.
84. Hirokawa et al., 1998, "SOSUI: classification and secondary structure prediction system for membrane proteins." Bioinformatics, 14: 378-379.
85. Hofmann & Stoffel, 1993, "TMbase—A database of membrane spanning proteins segments." Biol. Chem. Hoppe-Seyler, 374: 166.
86. Hoglund et al., 2006, "MultiLoc: prediction of protein subcellular localization using N-terminal targeting sequences, sequence motifs and amino acid composition." Bioinformatics, 22: 1158-1165.
87. Hooykaas-Van Slogteren et al., 1992, "Expression of Ti plasmid genes in monocotyledonous plants infected with *Agrobacterium tumefaciens*. 1984." Biotechnology, 24: 382-383.
88. Horsch et al., 1985, "A Simple and General Method for Transferring Genes into Plants Science 227: 1229-1231 (1985))."
89. Hsieh et al., 1998, "A PII-like protein in *Arabidopsis*: putative role in nitrogen sensing." Proc Natl Acad Sci USA, 95: 13965-13970.
90. Hu et al., 2000, "Human Ca2+ receptor cysteine-rich domain. Analysis of function of mutant and chimeric receptors." J Biol Chem, 275: 16382-16389.
91. Hudspeth et al., 1992, "Expression of Maize Phosphoenolpyruvate Carboxylase in Transgenic Tobacco: Effects on Biochemistry and Physiology." Plant Physiol, 98: 458-464.
92. Hudspeth et al., 1996, "Characterization and expression of metallothionein-like genes in cotton." Plant Mol Biol, 31: 701-705.
93. Huggins & Grant, 2005, "The function of the amino terminal domain in NMDA receptor modulation." Journal of Molecular Graphics and Modelling, 23: 381-388.
94. Jang et al., 1997, "Hexokinase as a sugar sensor in higher plants." Plant Cell, 9: 5-19.
95. Jang & Sheen, 1994, "Sugar sensing in higher plants." Plant Cell, 6: 1665-1679.
96. Kandt et al., 2006, "Opening and closing motions in the periplasmic vitamin B12 binding protein BtuF." Biochemistry, 45: 13284-13292.
97. Kang et al., 2006, "Overexpression in *Arabidopsis* of a plasma membrane-targeting glutamate receptor from small radish increases glutamate-mediated Ca2+ influx and delays fungal infection." Mol. Cells, 21: 418-427.
98. Kang et al., 2004, "The putative glutamate receptor 1.1 (AtGLR1.1) in *Arabidopsis thaliana* regulates abscisic acid biosynthesis and signaling to control development and water loss." Plant Cell Physiol., 45: 1380-1389.
99. Kang & Turano, 2003, "The putative glutamate receptor 1.1 (AtGLR1.1) functions as a regulator of carbon and nitrogen metabolism in *Arabidopsis thaliana*." PNAS, 100: 6872-6877.
100. Karnik et al., 2003, "Activation of G-protein-coupled receptors: a common molecular mechanism." Trends Endocrinol Metab, 14: 431-437.
101. Kaupmann et al., 2006. CH Patent No. 7119189.
102. Kaupmann et al., 1998, "GABA(B)-receptor subtypes assemble into functional heteromeric complexes." Nature, 396: 683-687.
103. Kelley et al., 2000, "Enhanced genome annotation using structural profiles in the program 3D-PSSM." J Mol Biol, 299: 499-520.

104. Kernytsky & Rost, 2003, "Static benchmarking of membrane helix predictions." Nucleic Acids Res, 31: 3642-3644.

105. Kim et al., 2001, "Overexpression of the AtGluR2 gene encoding an *Arabidopsis* homolog of mammalian glutamate receptors impairs calcium utilization and sensitivity to ionic stress in transgenic plants." Plant Cell Physiol, 42: 74-84.

106. Kirk & Othmer, 1993, "Concise Encyclopedia of Chemical Technology" (4th ed.): John Wiley & Sons.

107. Klein et al., 1988, "Transfer of foreign genes into intact maize cells with high-velocity microprojectiles." Proc Natl Acad Sci USA, 85: 4305-4309.

108. Klein et al., 1988, "Factors influencing gene delivery into *Zea mays* cells by high-velocity microprojectiles." Biotechnology, 6: 559-563

109. Kolakowski, 1994, "GCRDb: a G-protein-coupled receptor database." Receptors Channels, 2: 1-7.

110. Krens et al., 1982, "In Vitro transformation of plant protoplasts with Ti-plasmid DNA." Nature, 296: 72-74.

111. Kucho et al., 1999, "CO(2)-responsive transcriptional regulation of CAH1 encoding carbonic anhydrase is mediated by enhancer and silencer regions in *Chlamydomonas reinhardtii*." Plant Physiol, 121: 1329-1338.

112. Kucho et al., 2003, "Cis-acting elements and DNA-binding proteins involved in CO2-responsive transcriptional activation of Cah1 encoding a periplasmic carbonic anhydrase in *Chlamydomonas reinhardtii*." Plant Physiol, 133: 783-793.

113. Kyte & Doolittle, 1982, "A simple method for displaying the hydropathic character of a protein." J Mol Biol, 157: 105-132.

114. Lakowicz et al., 2001. U.S. Pat. No. 6,197,534.

115. Lam et al., 1998, "Glutamate-receptor genes in plants." Nature, 396: 125-126.

116. Langenheim & Thimann, 1982, "Botany: Plant biology and its relation to human affairs." John Wiley & Sons Inc.: New York.

117. Laursen et al., 1994, "Production of fertile transgenic maize by electroporation of suspension culture cells." Plant Mol. Biol., 24: 51-61

118. Lebel et al., 1998, "Functional analysis of regulatory sequences controlling PR-1 gene expression in *Arabidopsis*." Plant J, 16: 223-233.

119. Leubner-Metzger, et al., 1998, "Ethylene-responsive element binding protein (EREBP) expression and the transcriptional regulation of class I beta-1,3-glucanase during tobacco seed germination." Plant Mol Biol, 38: 785-795.

120. Lu et al., 1998, "Sugar response sequence in the promoter of a rice alpha-amylase gene serves as a transcriptional enhancer." J Biol Chem, 273: 10120-10131.

121. Madden 2002, "The structure and function of glutamate receptor ion channels." Nat Rev Neurosci, 3: 91-101.

122. Maniatis et al., 1985, "Molecular Cloning: A Laboratory Manual; DNA Cloning" (Vol. II). New York: Cold Spring Harbor.

123. Mano et al., 1996, "A Venus flytrap mechanism for activation and desensitization of alpha-amino-3-hydroxy-5-methyl-4-isoxazole propionic acid receptors." J Biol Chem, 271: 15299-15302.

124. Mao et al., 1982, "Hinge-bending in L-arabinose-binding protein. The "Venus's-flytrap" model." J Biol Chem, 257: 1131-1133.

125. Mayer, 2006, "Glutamate receptors at atomic resolution." Nature, 440: 456-462.

126. Mayer & Armstrong, 2004, "Structure and function of glutamate receptor ion channels." Annual Review of Physiology, 66: 161-181.

127. McCabe et al., 1988, "Stable transformation of soybean (*Glycine max*) by particle acceleration." Biotechnology, 6: 923-926.

128. McCammon et al., 1994, "An internal region of the peroxisomal membrane protein PMP47 is essential for sorting to peroxisomes." J Cell Biol, 124: 915-925.

129. Meinkoth, 1984, "Hybridization of nucleic acids immobilized on solid supports. Anal Biochem 1984; 138:267-84." Anal Biochem, 138: 267-284.

130. Meyerhoff et al., 2005, "AtGLR3.4, a glutamate receptor channel-like gene is sensitive to touch and cold." Planta, 222: 418-427.

131. Moon & Callahan, 2004, "Developmental regulation of peach ACC oxidase promoter-GUS fusions in transgenic tomato fruits." J Exper Bot, 55: 1519-1528.

132. Mosbach et al., 1983, "Formation of proinsulin by immobilized *Bacillus subtilis*." Nature, 302: 543-545.

133. Mulvihill et al., 1995. U.S. Pat. No. 5,385,831.

134. Murray et al., 1989, "Codon usage in plant genes." Nucleic Acids Res., 17: 477-498.

135. Myers & Miller, 1988, "Optimal alignments in linear-space." Computer Applic. Biol. Sci., 4: 11-17.

136. Natt et al., 2004, "Prediction of transmembrane regions of beta-barrel proteins using ANN- and SVM-based methods." Proteins, 56: 11-18.

137. Needleman & Wunsch, 1970, "A general method applicable to the search for similarities in the amino acid sequence of two proteins." J. Mol. Biol., 48: 443-453.

138. Newman et al., 1993, "DST sequences, highly conserved among plant SAUR genes, target reporter transcripts for rapid decay in tobacco." Plant Cell, 5: 701-714.

139. Ngai et al., 1997, "Light-induced transcriptional repression of the pea AS1 gene: identification of cis-elements and transfactors." Plant J, 12: 1021-1034.

140. O'Hara et al., 1993, "The ligand-binding domain in metabotropic glutamate receptors is related to bacterial periplasmic binding proteins." Neuron, 11: 41-52.

141. Ohgawara et al., 1983, "Uptake of liposome-encapsulated plasmid DNA by plant protoplasts and molecular fate of foreign DNA." Protoplasma, 116: 145-148.

142. Ohme-Takagi et al., 1993, "The effect of sequences with high AU content on mRNA stability in tobacco." Proc Natl Acad Sci USA, 90: 11811-11815.

143. Paek & Cho 2002. U.S. Pat. No. 6,478,938.

144. Paoletti et al., 2000, "Molecular organization of a zinc binding n-terminal modulatory domain in a NMDA receptor subunit." Neuron, 28: 911-925.

145. Parmentier et al., 1998, "The G protein-coupling profile of metabotropic glutamate receptors, as determined with exogenous G proteins, is independent of their ligand recognition domain." Mol Pharmacol, 53: 778-786.

146. Pasquier & Hamodrakas, 1999, "An hierarchical artificial neural network system for the classification of transmembrane proteins." Protein Eng, 12: 631-634.

147. Paszkowski et al., 1984, "Direct gene transfer to plants." Embo J, 3: 2717-2722.

148. Pathirana et al., 1997, "Analyses of phosphoenolpyruvate carboxylase gene structure and expression in alfalfa nodules." Plant J, 12: 293-304.

149. Pearson & Lipman, 1988, "Improved tools for biological sequence comparison." Proc Natl Acad Sci USA, 85: 2444-2448.

150. Pin et al., 2003, “Evolution, structure, and activation mechanism of family 3/C G-protein-coupled receptors.” Pharmacol Ther, 98: 325-354.
151. Pitner et al., 2006. U.S. Pat. No. 7,064,103.
152. Polge & Thomas, 2007, “SNF1/AMPK/SnRK1 kinases, global regulators at the heart of energy control?” Trends in Plant Science, 12: 20-28.
153. Potter et al., 2006, “Natriuretic peptides, their receptors, and cyclic guanosine monophosphate-dependent signaling functions.” Endocr Rev, 27: 47-72.
154. Qi et al., 2006, “Calcium entry mediated by GLR3.3, an *Arabidopsis* glutamate receptor with a broad agonist profile.” Plant Physiol., 142: 963-971.
155. Riggs & Bates, 1986, “Stable transformation of tobacco by electroporation: evidence for plasmid concatenation.” Proc Natl Acad Sci USA, 83: 5602-5606.
156. Rogers 1986, “Gene transfer in plants: Production of transformed plants using Ti-plasmid vectors.” Meth. Enzymol., 118: 627-640.
157. Rondard et al., 2006, “Coupling of agonist binding to effector domain activation in metabotropic glutamate-like receptors.” J Biol Chem, 281: 24653-24661.
158. Rusch & Kendall, 1995, “Protein transport via amino-terminal targeting sequences: common themes in diverse systems.” Mol Membr Biol, 12: 295-307.
159. Sanford et al. (1993). Optimizing the biolistic process for different biological application. In In: Wu R (ed) (Ed.), The Methods in Enzymology (Vol. 217, pp. 483-509). Orlando: Academic Press.
160. Schenk, 1996. U.S. Pat. No. 5,512,455.
161. Schwacke et al., 2003, “ARAMEMNON, a novel database for *Arabidopsis* integral membrane proteins.” Plant Physiol, 131: 16-26.
162. Servant et al., 2006. U.S. Pat. No. 7,022,488.
163. Shahin, 1985, “Totipotency of tomato protoplasts.” Theor. Appl. Genet, 69: 235-240.
164. Shatkay et al., 2007, “SherLoc: high-accuracy prediction of protein subcellular localization by integrating text and protein sequence data.” Bioinformatics, 23: 1410-1417.
165. Sheen & Jang, 2003. U.S. Pat. No. 6,632,602.
166. Sheen et al., 1999, “Sugars as signaling molecules.” Curr Opin Plant Biol, 2: 410-408.
167. Sherman, (1991). Getting started with yeast. In C. Guthrie & G. R. Fink (Eds.), Methods in Enzymology, Guide to Yeast Genetics and Molecular Biology (Vol. 194, pp. 3-21). New York: Acad. Press.
168. Sherman et al., 1982, “Methods in Yeast Genetics.” New York: Cold Spring Harbor Laboratory.
169. Shinmyo et al., 1998, “Metabolic engineering of cultured tobacco cells.” Biotechnol Bioeng, 58: 329-332.
170. Small et al., 2004, “Predotar: A tool for rapidly screening proteomes for N-terminal targeting sequences.” Proteomics, 4: 1581-1590.
171. Smeekens, 2000, “Sugar-induced signal transduction in plants.” Ann. Rev. Plant Physiol. Mol. Biol., 51: 49-81.
172. Smith & Waterman, 1981, “Comparison of biosequences.” Adv. Appl. Math, 2: 482-489.
173. Sohal et al., 1999, “The promoter of a *Brassica napus* lipid transfer protein gene is active in a range of tissues and stimulated by light and viral infection in transgenic *Arabidopsis*.” Plant Mol Biol, 41: 75-87.
174. Soll & Tien, 1998, “Protein translocation into and across the chloroplastic envelope membranes.” Plant Mol Biol, 38: 191-207.
175. Sporlein & Koop, 1991, “Lipofectin: direct gene transfer to higher plants using cationic liposomes.” Theor. Appl. Genet., 83: 1-5.
176. Stanier et al., 1986, “The microbial world, 5th ed.” New Jersey: Prentice-Hall.
177. Stolowitz et al., 2007a. U.S. Pat. No. 7,208,322.
178. Stolowitz et al., 2007b. U.S. Pat. No. 7,179,659.
179. Summers & Caguiat, 2004. U.S. Pat. No. 6,750,042.
180. Swinkels et al., 1991, “A novel, cleavable peroxisomal targeting signal at the amino-terminus of the rat 3-ketoacyl-CoA thiolase.” Embo J, 10: 3255-3262.
181. Thompson et al., 1995, “Maize transformation utilizing silicon carbide whiskers: a review.” Euphytica, 85: 75-80.
182. Tijssen, (1993). Overview of principles of hybridization and the strategy of nucleic acid probe assays. In Laboratory Techniques in Biochemistry and Molecular Biology—Hybridization with Nucleic Acid Probes, part I: Elsevier, New York.
183. Turano et al., 2001, “The putative glutamate receptors from plants are related to two superfamilies of animal neurotransmitter receptors via distinct evolutionary mechanisms.” Mol Biol Evol, 18: 1417-1420.
184. Tusnady & Simon, 1998, “Principles governing amino acid composition of integral membrane proteins: application to topology prediction.” J Mol Biol, 283: 489-506.
185. Tusnady & Simon, 2001, “The HMMTOP transmembrane topology prediction server.” Bioinformatics, 17: 849-850.
186. van Der Krol et al., 1999, “Developmental and wound-, cold-, desiccation-, ultraviolet-B-stress-induced modulations in the expression of the petunia zinc finger transcription factor gene ZPT2-2.” Plant Physiol, 121: 1153-1162.
187. Vasil, 1984, “Cell culture and somatic cell genetics of plants, Laboraory procedures and their applications ( )” (Vol. 1). Orlando: Academic Press.
188. von Heijne, 1986, “Mitochondrial targeting sequences may form amphiphilic helices.” EMBO J, 5: 1335-1342.
189. von Heijne, 1992, “Membrane protein structure prediction, hydrophobicity analysis and the positive-inside rule.” J. Mol. Biol., 225: 487-494.
190. Watson et al., 1992, “Recombinant DNA.” New York: Scientific American Books.
191. Wollmuth & Sobolevsky, 2004, “Structure and gating of the glutamate receptor ion channel.” TRENDS in Neurosciences, 27: 321-328.
192. Wootton & Federhen, 1993, “Statistics of local complexity in amino acid sequences and sequence databases.” Comput. Chem., 17: 149-163.
193. Wootton & Federhen, 1996, “Analysis of compositionally biased regions in sequence databases.” Methods Enzymol, 266: 554-571.
194. Wu et al., 2007, “Functional analysis of a cotton glucuronosyltransferase promoter in transgenic tobaccos.” Cell Research 17: 174-183.
195. Xu et al., 2004, “Different functional roles of T1R subunits in the heteromeric taste receptors.” Proc Natl Acad Sci USA, 101: 14258-14263.
196. Yan et al., 2004. U.S. Pat. No. 6,830,900.
197. Yanagawa et al., 2005. U.S. Pat. No. 6,977,160.
198. Yang et al., 2002, “Isolation and characterization of the orchid cytokinin oxidase DSCKX1 promoter.” J. Exper, Bot., 53: 1899-1907.
199. Yuan et al., 2005, “The institute for genomic research Osal rice genome annotation database.” Plant Physiol, 138: 18-26.

200. Zheng et al., 2001, "Allosteric interaction between the amino terminal domain and the ligand binding domain of NR2A." Nat Neurosci, 4: 894-901.
201. Broothaerts et al., 2005, "Gene transfer to plants by diverse species of bacteria." Nature 433:629-633.
202. Szewczyk et al., 2006, "Fusion PCR and gene targeting in *Aspergillus nidulans*." Nature Protocols 1:3111-3120.
203. Ho et al., 1989, "Site-directed mutagenesis by overlap extension using the polymerase chain reaction." Gene 77:51-59.
204. Li, et al., 2006. "Oil content of *Arabidopsis* seeds: The influence of seed anatomy, light and plant-to-plant variation." Phytochemistry, 67: 904-915.
205. Joshi, et al., 1997. "Context sequences of translation codons in plants." Plant Mol Biol 35:993-1001.
206. Sawant, et al., 2001. "Sequence architecture downstream of the initiator codon enhance gene expression and protein stability in plant." Plant Physiol 126:1630-1636.

The invention claimed is:

1. A transgenic plant comprising a nucleic acid encoding a fusion protein wherein the fusion protein comprises:

(a) a first polypeptide segment comprising a first bacterial periplasmic binding protein (bPBP); and (b) a second polypeptide segment comprising a second bPBP, and (c) optionally a transit peptide, wherein the N terminus of the second polypeptide segment is linked to the C terminus of the first polypeptide segment, wherein the C terminus of the optional transit peptide is linked to the N terminus of the first polypeptide segment, wherein the second polypeptide segment is the C terminus of the fusion protein, wherein the optional transit peptide or the first polypeptide segment is the N terminus of the fusion protein, and wherein each bPBP binds to a specific ligand and controls the availability of the ligand to a cell, and wherein the transgenic plant comprising the fusion protein has an altered metabolism relative to a corresponding control plant that does not comprise the fusion protein.

2. The transgenic plant of claim 1, wherein the plant has increased seed weight.

3. The transgenic plant of claim 1, wherein the plant has increased seed oil content.

4. The transgenic plant of claim 1, wherein the plant has increased lignin.

5. The transgenic plant of claim 1, wherein the plant has increased sugar content.

6. The transgenic plant of claim 1, wherein the plant has increased cellulose.

7. The transgenic plant of claim 1, wherein the plant has increased oil.

8. The transgenic plant of claim 1, wherein the fusion protein includes the transit peptide.

9. The transgenic plant of claim 1, wherein the plant is selected from the group consisting of *acacia*, alfalfa, aneth, apple, apricot, artichoke, arugula, asparagus, avocado, banana, barley, beans, beech, beet, Bermuda grass, blackberry, blueberry, Blue grass, broccoli, brussels sprouts, cabbage, camelina, canola, cantaloupe, carrot, cassava, cauliflower, celery, cherry, chicory, cilantro, citrus, clementines, coffee, corn, cotton, cucumber, duckweed, Douglas fir, eggplant, endive, escarole, eucalyptus, fennel, fescue, figs, forest trees, garlic, gourd, grape, grapefruit, honey dew, jatropha, jicama, kiwifruit, lettuce, leeks, lemon, lime, Loblolly pine, maize, mango, melon, mushroom, nectarine, nut, oat, okra, onion, orange, an ornamental plant, palm, papaya, parsley, pea, peach, peanut, pear, pepper, persimmon, pine, pineapple, plantain, plum, pomegranate, poplar, potato, pumpkin, quince, radiata pine, radicchio, radish, rapeseed, raspberry, rice, rye, rye grass, scallion, sorghum, Southern pine, soybean, spinach, squash, strawberry, sugarbeet, sugarcane, sunflower, sweet potato, sweetgum, switchgrass, tangerine, tea, tobacco, tomato, turf, turnip, a vine, watermelon, wheat, yams, and zucchini.

10. The transgenic plant of claim 1, wherein the first bPBP is selected from the group consisting of periplasmic glucose-galactose-binding proteins (GGBP), periplasmic leucine-isoleucine-valine-binding proteins, periplasmic glycerol-3-phosphate-binding proteins, periplasmic lysine-arginine-ornithine-binding proteins, periplasmic glutamine-binding proteins (QBP), periplasmic glutamate-binding proteins (GluBP), periplasmic C4-dicarboxylate-binding protein, periplasmic dicarboxylate-binding protein, periplasmic succinate-malate-fumarate binding protein, periplasmic putrescine-spermidine-binding protein, periplasmic polyamine-binding protein, and periplasmic glutamate-aspartate binding protein.

11. The transgenic plant of claim 1, wherein the second bPBP is selected from the group consisting of periplasmic glucose-galactose-binding proteins (GGBP), periplasmic leucine-isoleucine-valine-binding proteins, periplasmic glycerol-3-phosphate-binding proteins, periplasmic lysine-arginine-ornithine-binding proteins, periplasmic glutamine-binding proteins (QBP), periplasmic glutamate-binding proteins (GluBP), periplasmic C4-dicarboxylate-binding protein, periplasmic dicarboxylate-binding protein, periplasmic succinate-malate-fumarate binding protein, periplasmic putrescine-spermidine-binding protein, periplasmic polyamine-binding protein, and periplasmic glutamate-aspartate binding protein.

12. The transgenic plant of claim 1, wherein the first polypeptide segment comprises a third bPBP.

13. The transgenic plant of claim 12, wherein the third bPBP is selected from the group consisting of periplasmic glucose-galactose-binding proteins (GGBP), periplasmic leucine-isoleucine-valine-binding proteins, periplasmic glycerol-3-phosphate-binding proteins, periplasmic lysine-arginine-ornithine-binding proteins, periplasmic glutamine-binding proteins (QBP), periplasmic glutamate-binding proteins (GluBP), periplasmic C4-dicarboxylate-binding protein, periplasmic dicarboxylate-binding protein, periplasmic succinate-malate-fumarate binding protein, periplasmic putrescine-spermidine-binding protein, periplasmic polyamine-binding protein, and periplasmic glutamate-aspartate binding protein.

14. A method of controlling the availability of metabolites to a plant cell, said method comprising the step of contacting the transgenic plant of claim 1 expressing the fusion protein with an amino acid, thereby controlling the availability of metabolites to the plant cell.

15. A method of controlling the availability of metabolites to a plant cell, said method comprising the step of growing the transgenic plant of claim 1 under conditions suitable for the expression of the fusion protein by the transgenic plant, thereby controlling the availability of metabolites to the transgenic plant.

* * * * *

SEQUENCE LISTING

<160> NUMBER OF SEQ ID NOS: 51

<210> SEQ ID NO 1
<211> LENGTH: 32
<212> TYPE: DNA
<213> ORGANISM: Artificial Sequence
<220> FEATURE:
<223> OTHER INFORMATION: primer

<400> SEQUENCE: 1
ttttgaattc cacatttgca aaatgatgaa tg 32

<210> SEQ ID NO 2
<211> LENGTH: 32
<212> TYPE: DNA
<213> ORGANISM: Artificial Sequence
<220> FEATURE:
<223> OTHER INFORMATION: primer

<400> SEQUENCE: 2
ttttgagctc ccaatctggt taccgcattg ac 32

<210> SEQ ID NO 3
<211> LENGTH: 32
<212> TYPE: DNA
<213> ORGANISM: Artificial Sequence
<220> FEATURE:
<223> OTHER INFORMATION: primer

<400> SEQUENCE: 3
ttttgagctc atgaaaaaat ggtcacgcca cc 32

<210> SEQ ID NO 4
<211> LENGTH: 29
<212> TYPE: DNA
<213> ORGANISM: Artificial Sequence
<220> FEATURE:
<223> OTHER INFORMATION: primer

<400> SEQUENCE: 4
ttttggtacc acgtcctgct ttcagcttc 29

<210> SEQ ID NO 5
<211> LENGTH: 32
<212> TYPE: DNA

<213> ORGANISM: Artificial Sequence
<220> FEATURE:
<223> OTHER INFORMATION: primer

<400> SEQUENCE: 5
ttttggtacc ttttttggca tagccgcttt gt 32

<210> SEQ ID NO 6
<211> LENGTH: 35
<212> TYPE: DNA
<213> ORGANISM: Artificial Sequence
<220> FEATURE:
<223> OTHER INFORMATION: primer

<400> SEQUENCE: 6
tttttctaga ttataaccaa attaaattcc ccacc 35

<210> SEQ ID NO 7
<211> LENGTH: 32
<212> TYPE: DNA
<213> ORGANISM: Artificial Sequence
<220> FEATURE:
<223> OTHER INFORMATION: primer

<400> SEQUENCE: 7
tttttctaga taccgagctc gaatttcccc ga 32

<210> SEQ ID NO 8
<211> LENGTH: 32
<212> TYPE: DNA
<213> ORGANISM: Artificial Sequence
<220> FEATURE:
<223> OTHER INFORMATION: primer

<400> SEQUENCE: 8
ttttctgcag gatctagtaa catagatgac ac 32

<210> SEQ ID NO 9
<211> LENGTH: 32
<212> TYPE: DNA
<213> ORGANISM: Artificial Sequence
<220> FEATURE:
<223> OTHER INFORMATION: primer

<400> SEQUENCE: 9
ttttgaattc tcatacatat tcatacttga tg 32

<210> SEQ ID NO 10
<211> LENGTH: 32
<212> TYPE: DNA
<213> ORGANISM: Artificial Sequence
<220> FEATURE:
<223> OTHER INFORMATION: primer

<400> SEQUENCE: 10
ttttgagctc ataatttctt gtatagctct gt 32

<210> SEQ ID NO 11
<211> LENGTH: 32
<212> TYPE: DNA
<213> ORGANISM: Artificial Sequence
<220> FEATURE:
<223> OTHER INFORMATION: primer

<400> SEQUENCE: 11
ttttggatcc taaccaaatt aaattcccca cc 32

<210> SEQ ID NO 12
<211> LENGTH: 32
<212> TYPE: DNA
<213> ORGANISM: Artificial Sequence
<220> FEATURE:
<223> OTHER INFORMATION: primer

<400> SEQUENCE: 12
ttttggatcc atgtacgagt ttgactggag tt 32

<210> SEQ ID NO 13
<211> LENGTH: 32
<212> TYPE: DNA
<213> ORGANISM: Artificial Sequence
<220> FEATURE:
<223> OTHER INFORMATION: primer

<400> SEQUENCE: 13
tttttctaga ttatgctgtc cttcttttca ag 32

<210> SEQ ID NO 14
<211> LENGTH: 32
<212> TYPE: DNA
<213> ORGANISM: Artificial Sequence
<220> FEATURE:
<223> OTHER INFORMATION: primer

<400> SEQUENCE: 14
ttttggtacc atgtacgagt ttgactggag tt 32

<210> SEQ ID NO 15
<211> LENGTH: 32
<212> TYPE: DNA
<213> ORGANISM: Artificial Sequence
<220> FEATURE:
<223> OTHER INFORMATION: primer

<400> SEQUENCE: 15
ttttggtacc cacatttgca aaatgatgaa tg 32

<210> SEQ ID NO 16
<211> LENGTH: 32
<212> TYPE: DNA
<213> ORGANISM: Artificial Sequence
<220> FEATURE:
<223> OTHER INFORMATION: primer

<400> SEQUENCE: 16
ttttctgcag ccaatctggt taccgcattg ac 32

<210> SEQ ID NO 17
<211> LENGTH: 32
<212> TYPE: DNA
<213> ORGANISM: Artificial Sequence
<220> FEATURE:
<223> OTHER INFORMATION: primer

<400> SEQUENCE: 17
ttttctgcag atgggcccgg ggggaccctg ta 32

<210> SEQ ID NO 18
<211> LENGTH: 32
<212> TYPE: DNA
<213> ORGANISM: Artificial Sequence
<220> FEATURE:
<223> OTHER INFORMATION: primer

<400> SEQUENCE: 18
ttttgctagc ctgagacagg aaacggaatg tc 32

<210> SEQ ID NO 19
<211> LENGTH: 32
<212> TYPE: DNA
<213> ORGANISM: Artificial Sequence
<220> FEATURE:
<223> OTHER INFORMATION: primer

<400> SEQUENCE: 19
ttttgctagc atgttgaccc gtcgtatcct tg 32

<210> SEQ ID NO 20
<211> LENGTH: 32
<212> TYPE: DNA
<213> ORGANISM: Artificial Sequence
<220> FEATURE:
<223> OTHER INFORMATION: primer

<400> SEQUENCE: 20
ttttggatcc ttattccgcc gtcgcggcct tg 32

<210> SEQ ID NO 21
<211> LENGTH: 32
<212> TYPE: DNA
<213> ORGANISM: Artificial Sequence
<220> FEATURE:
<223> OTHER INFORMATION: primer

<400> SEQUENCE: 21
ttttggatcc taccgagctc gaatttcccc ga 32

<210> SEQ ID NO 22
<211> LENGTH: 32
<212> TYPE: DNA
<213> ORGANISM: Artificial Sequence
<220> FEATURE:
<223> OTHER INFORMATION: primer

<400> SEQUENCE: 22
tttttctaga gatctagtaa catagatgac ac 32

<210> SEQ ID NO 23
<211> LENGTH: 25
<212> TYPE: DNA
<213> ORGANISM: Artificial Sequence
<220> FEATURE:
<223> OTHER INFORMATION: primer

<400> SEQUENCE: 23
tctttatgta acaatgagtc gatgg 25

<210> SEQ ID NO 24
<211> LENGTH: 45
<212> TYPE: DNA
<213> ORGANISM: Artificial Sequence
<220> FEATURE:
<223> OTHER INFORMATION: primer

<400> SEQUENCE: 24
gatttgacca taagcagcca tgtcttcaaa ctctaggaac ttttc 45

<210> SEQ ID NO 25
<211> LENGTH: 21
<212> TYPE: DNA

-continued

<213> ORGANISM: Artificial Sequence
<220> FEATURE:
<223> OTHER INFORMATION: primer

<400> SEQUENCE: 25
atggctgctt atggtcaaat c 21

<210> SEQ ID NO 26
<211> LENGTH: 22
<212> TYPE: DNA
<213> ORGANISM: Artificial Sequence
<220> FEATURE:
<223> OTHER INFORMATION: primer

<400> SEQUENCE: 26
gattttaatc gatctaacgg ag 22

<210> SEQ ID NO 27
<211> LENGTH: 40
<212> TYPE: DNA
<213> ORGANISM: Artificial Sequence
<220> FEATURE:
<223> OTHER INFORMATION: primer

<400> SEQUENCE: 27
ctccgttaga tcgattaaaa tcgcaggcag cacgctggac 40

<210> SEQ ID NO 28
<211> LENGTH: 44
<212> TYPE: DNA
<213> ORGANISM: Artificial Sequence
<220> FEATURE:
<223> OTHER INFORMATION: primer

<400> SEQUENCE: 28
ggaaattcga gctcggtagc ctacagatct tcttcagaaa taag 44

<210> SEQ ID NO 29
<211> LENGTH: 20
<212> TYPE: DNA
<213> ORGANISM: Artificial Sequence
<220> FEATURE:
<223> OTHER INFORMATION: primer

<400> SEQUENCE: 29
gctaccgagc tcgaatttcc 20

<210> SEQ ID NO 30
<211> LENGTH: 20
<212> TYPE: DNA
<213> ORGANISM: Artificial Sequence
<220> FEATURE:
<223> OTHER INFORMATION: primer

<400> SEQUENCE: 30
ttaagttggg taacgccagg 20

<210> SEQ ID NO 31
<211> LENGTH: 30
<212> TYPE: DNA
<213> ORGANISM: Artificial Sequence
<220> FEATURE:
<223> OTHER INFORMATION: primer

<400> SEQUENCE: 31
ttttggtacc aagatggagg gcagtaggtg 30

<210> SEQ ID NO 32
<211> LENGTH: 31
<212> TYPE: DNA
<213> ORGANISM: Artificial Sequence
<220> FEATURE:
<223> OTHER INFORMATION: primer

<400> SEQUENCE: 32
ttttaagctt cccgatctag taacatagat g 31

<210> SEQ ID NO 33
<211> LENGTH: 20
<212> TYPE: DNA
<213> ORGANISM: Artificial Sequence
<220> FEATURE:
<223> OTHER INFORMATION: primer

<400> SEQUENCE: 33
taatacgact cactataggg 20

<210> SEQ ID NO 34
<211> LENGTH: 52
<212> TYPE: DNA
<213> ORGANISM: Artificial Sequence
<220> FEATURE:
<223> OTHER INFORMATION: primer

<400> SEQUENCE: 34
cttcttccgc gttaacttcg ccttcagtac tgttcagtgc cttgtcattc gg 52

<210> SEQ ID NO 35
<211> LENGTH: 20
<212> TYPE: DNA
<213> ORGANISM: Artificial Sequence
<220> FEATURE:
<223> OTHER INFORMATION: primer

<400> SEQUENCE: 35
attaaccctc actaaaggga 20

<210> SEQ ID NO 36
<211> LENGTH: 46
<212> TYPE: DNA
<213> ORGANISM: Artificial Sequence
<220> FEATURE:
<223> OTHER INFORMATION: primer

<400> SEQUENCE: 36
cgaagttaac gcggaagaag aaggctttgc aggcagcacg ctggac 46

<210> SEQ ID NO 37
<211> LENGTH: 24
<212> TYPE: DNA
<213> ORGANISM: Artificial Sequence
<220> FEATURE:
<223> OTHER INFORMATION: primer

<400> SEQUENCE: 37
gatcatacat attcatactt gatg 24

<210> SEQ ID NO 38
<211> LENGTH: 45
<212> TYPE: DNA
<213> ORGANISM: Artificial Sequence
<220> FEATURE:
<223> OTHER INFORMATION: primer -continued

<400> SEQUENCE: 38
ctctttaggt ttcgtgccat ataatttctt gtatagctct gtaac 45

<210> SEQ ID NO 39
<211> LENGTH: 20
<212> TYPE: DNA
<213> ORGANISM: Artificial Sequence
<220> FEATURE:
<223> OTHER INFORMATION: primer

<400> SEQUENCE: 39
atggcacgaa acctaaagag 20

<210> SEQ ID NO 40
<211> LENGTH: 19
<212> TYPE: DNA
<213> ORGANISM: Artificial Sequence
<220> FEATURE:
<223> OTHER INFORMATION: primer

<400> SEQUENCE: 40
agcgtaggct cggtcaacg 19

<210> SEQ ID NO 41
<211> LENGTH: 37
<212> TYPE: DNA
<213> ORGANISM: Artificial Sequence
<220> FEATURE:
<223> OTHER INFORMATION: primer

<400> SEQUENCE: 41
cgttgaccga gcctacgctg caggcagcac gctggac 37

<210> SEQ ID NO 42
<211> LENGTH: 44
<212> TYPE: DNA
<213> ORGANISM: Artificial Sequence
<220> FEATURE:
<223> OTHER INFORMATION: primer

<400> SEQUENCE: 42
ggaaattcga gctcggtagc ctacagatct tcttcagaaa taag 44

<210> SEQ ID NO 43
<211> LENGTH: 30
<212> TYPE: DNA
<213> ORGANISM: Artificial Sequence
<220> FEATURE:
<223> OTHER INFORMATION: primer

<400> SEQUENCE: 43
ttttggtacc cgaagctcaa tcgtctcgag 30

<210> SEQ ID NO 44
<211> LENGTH: 1418
<212> TYPE: DNA
<213> ORGANISM: Arabidopsis thaliana

<400> SEQUENCE: 44
agatggaggg cagtaggtgt gacggctgag agtctattcc cgtgtttcaa taattaagtg 60
atttatttta aataataata atggtaaatt tgaactgatg ttttttttg ggattttgat 120 ttgagtttcg atttggcgat tttgtctcgt ttcaactgac aaaacaatgt cgtttagata 180
caacagagac gactaacagg agtttaatat cgtaaaagtt tttaattagt ctactaaaca 240

-continued

```
ccatgcctaa gtgactggtc aatcaaactt tgtcatttaa acttaaagtt aaccaaaatt    300

ttacgatttt aaatttattt gtcttcctcg tagtttatga tttaatcgtc ccaaattcaa    360

aaattcgtat ttttttgttg acatttttac ctttttctta ctaacaaagt aacaatgtga    420

ccgtgataca cgatagatca ttaatggaac tgttcaaaaa tataaaaagt accaaaaaac    480

ttcttaaaag ttaatcatac agtcagtcca aacggtttaa tcttcataaa gatttttaa    540

aacgagtctc aaaatcactt ttctaatttt ctagcggatg aaccatgttt tggtcatgag    600

aaactgacaa atcatttcat gtatctgtaa aacgcctaac atcacaatgc gaatgaagat    660

gttgtttaat caaacaccga atgaattcca cgaagcagat cgccttatta tgatcaaaag    720

agccccacat tcgcgttcgt atgtcctcta ccctatccaa gcactattct tctttaaata    780

tagctagaac catctcaagc atgttcaagc caaggcgact aaaaaagcag tttaaatcca    840

tcttgattta aatatgtttt tggctcaaaa gaaaagaatg taatgttatg gcctgtttct    900

ttgaagaaaa cgatataaca aattattctg ttagtatatt tattttttac cataacatgt    960

cattttatgt tattcaaaaa tgttatacgg tacaaatgtt attctattag tacgtatatc   1020

tacattgaca caccatgcat tctccatttt aacgttcaat aacgatcagt caattaaatt   1080

ggtctttagt cttttagaat tttatatatc tattcgatta ttaagatgat atataattaa   1140

aaaaaagatt ggaggggtaa ccgaaaatga gaattagtaa ttccctaggt aggttaaaat   1200

ttagaattag taaatcatta ttttccacgt tttcatgcat gattgccata tgtatgaacg   1260

tgtattaata aaaccaaact taaaaacttg tccgttacaa ctacatctat ataacagcag   1320

ttctaccatc ctgaaaatca aatcacattc tcaaatacac attttaagaa agaaaaaaaa   1380

aaattgaaag ttgagaaaag ttcctagagt ttgaagac                           1418


<210> SEQ ID NO 45
<211> LENGTH: 1143
<212> TYPE: DNA
<213> ORGANISM: Brassica napus

<400> SEQUENCE: 45

tcttcatcgg tgattgattc ctttaaagac ttatgtttct tatcttgctt ctgaggcaag     60

tattcagtta ccagttacca cttatattct ggactttctg actgcatcct catttttcca    120

acattttaaa tttcactatt ggctgaatgc ttcttctttg aggaagaaac aattcagatg    180

gcagaaatgt atcaaccaat gcatatatac aaatgtacct cttgttctca aaacatctat    240

cggatggttc catttgcttt gtcatccaat tagtgactac tttatattat tcactcctct    300

ttattactat tttcatgcga ggttgccatg tacattatat ttgtaaggat tgacgctatt    360

gagcgttttt cttcaatttt ctttatttta gacatgggta tgaaatgtgt gttagagttg    420

ggttgaatga gatatacgtt caagtgaagt ggcataccgt tctcgagtaa ggatgaccta    480

cccattcttg agacaaatgt tacattttag tatcagagta aaatgtgtac ctataactca    540

aattcgattg acatgtatcc attcaacata aaattaaacc agcctgcacc tgcatccaca    600

tttcaagtat tttcaaaccg ttcggctcct atccaccggg tgtaacaaga cggattccga    660

atttggaaga ttttgactca aattcccaat ttatattgac cgtgactaaa tcaactttaa    720

cttctataat tctgattaag ctcccaattt atattcccaa cggcactacc tccaaaattt    780

atagactctc atccccttttt aaaccaactt agtaaacgtt ttttttttta attttatgaa    840

gttaagtttt taccttgttt ttaaaaagaa tcgttcataa gatgccatgc cagaacatta    900

gctacacgtt acacatagca tgcagccgcg gagaattgtt tttcttcgcc acttgtcact    960
```

-continued cccttcaaac acctaagagc ttctctctca cagcacacac atacaatcac atgcgtgcat 1020
gcattattac acgtgatcgc catgcaaatc tcctttatag cctataaatt aactcatccg 1080
cttcactctt tactcaaacc aaaactcatc aatacaaaca agattaaaaa catacacgag 1140
ctc 1143

<210> SEQ ID NO 46
<211> LENGTH: 612
<212> TYPE: DNA
<213> ORGANISM: Glycine max

<400> SEQUENCE: 46
ttttgatcca tgcccttcat ttgccgctta ttaattaatt tggtaacagt ccgtactaat 60
cagttactta tccttccccc atcataatta atcttggtag tctcgaatgc cacaacactg 120
actagtctct tggatcataa gaaaaagcca aggaacaaaa gaagacaaaa cacaatgaga 180
gtatcctttg catagcaatg tctaagttca taaaattcaa acaaaaaacgc aatcacacac 240 agtggacatc acttatccac tagctgatca ggatcgccgc gtcaagaaaa aaaaactgga 300
ccccaaaagc catgcacaac aacacgtact cacaaaggtg tcaatcgagc agcccaaaac 360
attcaccaac tcaacccatc atgagccctc acatttgttg tttctaaccc aacctcaaac 420
tcgtattctc ttccgccacc tcatttttgt ttatttcaac acccgtcaaa ctgcatgcca 480
ccccgtggcc aaatgtccat gcatgttaac aagacctatg actataaata gctgcaatct 540
cggcccaggt tttcatcatc aagaaccagt tcaatatcct agtacaccgt attaaagaat 600
ttaagatata ct 612

<210> SEQ ID NO 47
<211> LENGTH: 1557
<212> TYPE: DNA
<213> ORGANISM: Phaseolus vulgaris

<400> SEQUENCE: 47
ggcgcgccca ttgtactccc agtatcatta tagtgaaagt tttggctctc tcgccggtgg 60
ttttttacct ctatttaaag gggttttcca cctaaaaatt ctggtatcat tctcacttta 120
cttgttactt taatttctca taatctttgg ttgaaattat cacgcttccg cacacgatat 180
ccctacaaat ttattatttg ttaaacattt tcaaaccgca taaaatttta tgaagtcccg 240
tctatcttta atgtagtcta acattttcat attgaaatat ataatttact taattttagc 300
gttggtagaa agcataaaga tttattctta ttcttcttca tataaatgtt taatatacaa 360
tataaacaaa ttctttacct taagaaggat ttcccatttt atattttaaa aatatattta 420
tcaaatattt ttcaaccacg taaatctcat aataataagt tgtttcaaaa gtaataaaat 480
ttaactccat aattttttta ttcgactgat cttaaagcaa cacccagtga cacaactagc 540 cattttttttc tttgaataaa aaaatccaat tatcattgta tttttttat acaatgaaaa 600 tttcaccaaa caatcatttg tggtatttct gaagcaagtc atgttatgca aaattctata 660
attcccattt gacactacgg aagtaactga agatctgctt ttacatgcga gacacatctt 720
ctaaagtaat tttaataata gttactatat tcaagatttc atatatcaaa tactcaatat 780
tacttctaaa aaattaatta gatataatta aaatattact tttttaattt taagtttaat 840
tgttgaattt gtgactattg atttattatt ctactatgtt taaattgttt tatagatagt 900
ttaaagtaaa tataagtaat gtagtagagt gttagagtgt taccctaaac cataaactat 960
aagatttatg gtggactaat tttcatatat ttcttattgc ttttaccttt tcttggtatg 1020
taagtccgta actagaatta cagtgggttg tcatggcact ctgtggtctt ttggttcatg 1080
catgggtctt gcgcaagaaa aagacaaaga acaaagaaaa aagacaaaac agagagacaa 1140
aacgcaatca cacaaccaac tcaaattagt cactggctga tcaagatcgc cgcgtccatg 1200
tatgtctaaa tgccatgcaa agcaacacgt gcttaacatg cactttaaat ggctcaccca 1260
tctcaaccca cacacaaaca cattgccttt ttcttcatca tcaccacaac cacctgtata 1320
tattcattct cttccgccac ctcaatttct tcacttcaac acacgtcaac ctgcatatgc 1380
gtgtcatccc atgcccaaat ctccatgcat gttccaacca ccttctctct tatataatac 1440
ctataaatac ctctaatatc actcacttct ttcatcatcc atccatccag agtactacta 1500
ctctactact ataatacccc aacccaactc atattcaata ctactctact taattaa 1557

<210> SEQ ID NO 48
<211> LENGTH: 837
<212> TYPE: DNA
<213> ORGANISM: Artificial Sequence
<220> FEATURE:
<223> OTHER INFORMATION: Synthetic Construct

<400> SEQUENCE: 48
atggcttcct ctgctggatc tactcttgat aagatcgcta agaacggtgt tatcgttgtg 60
ggacatagag agtcatctgt ccctttcagc tactacgata accagcagaa ggttgtcgga 120
tactctcagg attactctaa cgctatcgtt gaggctgtga agaagaagct caacaagcct 180
gatctccagg ttaagctcat ccctatcacc tctcagaaca gaatccctct tcttcaaaac 240
ggaaccttcg atttcgagtg cggatctact actaacaacg ctgagagaca aaagcaggct 300
gctttctctg ataccatctt cgttgttgga accagacttc ttaccaagaa aggtggtgac 360
atcaaggatt tcgctgatct taagggaaag gctgttgttg ttacttctgg aactacctct 420
gaggttctcc ttaacaaact taacgaggaa caaaagatga acatgaggat catcagcgct 480
aaggatcacg gtgattcttt cagaactctc gagtctggta gagctgttgc ttttatgatg 540
gatgatgctc tccttgctgg tgagagagct aaggctaaga agcctgataa ctgggagatc 600
gttggaaagc ctcaatctca agaggcttac ggatgcatgc tcagaaagga tgatccacag 660
ttcaagaaac tcatggacga tacaatcgct caggttcaaa cttctggtga ggctgagaag 720
tggttcgata agtggttcaa gaaccctatc cctcctaaga acctcaacat gaacttcgag 780
cttagcgacg agatgaaggc tctcttcaaa gagcctaacg acaaggctct caactag 837

<210> SEQ ID NO 49
<211> LENGTH: 1002
<212> TYPE: DNA
<213> ORGANISM: Artificial Sequence
<220> FEATURE:
<223> OTHER INFORMATION: Synthetic Construct

<400> SEQUENCE: 49
atggctgctt atggacaaat ttcttctgga atgactgttg atcctcaagt tttgtcttct 60
tctagaaata ttggagtttc tttgtctcct ttgagaagaa ctttgattgg agctggagtt 120
agatctactt ctatttcttt gagacaatgt tctttgtctg ttagatctat taagattgct 180
ggatctactc ttgataagat cgctaagaac ggtgttatcg ttgtgggaca tagagagtca 240
tctgtccctt tcagctacta cgataaccag cagaaggttg tcggatactc tcaggattac 300
tctaacgcta tcgttgaggc tgtgaagaag aagctcaaca agcctgatct ccaggttaag 360
ctcatcccta tcacctctca gaacagaatc cctcttcttc aaaacggaac cttcgatttc 420

-continued gagtgcggat ctactactaa caacgctgag agacaaaagc aggctgcttt ctctgatacc 480
atcttcgttg ttggaaccag acttcttacc aagaaaggtg gtgacatcaa ggatttcgct 540
gatcttaagg gaaaggctgt tgttgttact tctggaacta cctctgaggt tctccttaac 600
aaacttaacg aggaacaaaa gatgaacatg aggatcatca gcgctaagga tcacggtgat 660
tctttcagaa ctctcgagtc tggtagagct gttgctttta tgatggatga tgctctcctt 720
gctggtgaga gagctaaggc taagaagcct gataactggg agatcgttgg aaagcctcaa 780
tctcaagagg cttacggatg catgctcaga aaggatgatc cacagttcaa gaaactcatg 840
gacgatacaa tcgctcaggt tcaaacttct ggtgaggctg agaagtggtt cgataagtgg 900
ttcaagaacc ctatccctcc taagaacctc aacatgaact tcgagcttag cgacgagatg 960
aaggctctct tcaaagagcc taacgacaag gctctcaact ag 1002

<210> SEQ ID NO 50
<211> LENGTH: 903
<212> TYPE: DNA
<213> ORGANISM: Artificial Sequence
<220> FEATURE:
<223> OTHER INFORMATION: Synthetic Construct

<400> SEQUENCE: 50
atggcacgaa acctaaagag catgatgctt tgtgggtttg gtctcttgtg ttttcttatg 60
atcgttgacc gagcctacgc tggatctact cttgataaga tcgctaagaa cggtgttatc 120
gttgtgggac atagagagtc atctgtccct ttcagctact acgataacca gcagaaggtt 180
gtcggatact ctcaggatta ctctaacgct atcgttgagg ctgtgaagaa gaagctcaac 240
aagcctgatc tccaggttaa gctcatccct atcacctctc agaacagaat ccctcttctt 300
caaaacggaa ccttcgattt cgagtgcgga tctactacta acaacgctga gagacaaaag 360
caggctgctt tctctgatac catcttcgtt gttggaacca gacttcttac caagaaaggt 420
ggtgacatca aggatttcgc tgatcttaag ggaaaggctg ttgttgttac ttctggaact 480
acctctgagg ttctccttaa caaacttaac gaggaacaaa agatgaacat gaggatcatc 540
agcgctaagg atcacggtga ttctttcaga actctcgagt ctggtagagc tgttgctttt 600
atgatggatg atgctctcct tgctggtgag agagctaagg ctaagaagcc tgataactgg 660
gagatcgttg gaaagcctca atctcaagag gcttacggat gcatgctcag aaaggatgat 720
ccacagttca agaaactcat ggacgataca atcgctcagg ttcaaacttc tggtgaggct 780
gagaagtggt tcgataagtg gttcaagaac cctatccctc ctaagaacct caacatgaac 840
ttcgagctta gcgacgagat gaaggctctc ttcaaagagc ctaacgacaa ggctctcaac 900
tag 903

<210> SEQ ID NO 51
<211> LENGTH: 1059
<212> TYPE: DNA
<213> ORGANISM: Artificial Sequence
<220> FEATURE:
<223> OTHER INFORMATION: Synthetic Construct

<400> SEQUENCE: 51
atggctagaa atttgaagtc tatgatgttg tgtggatttg gattgttgtg ttttttgatg 60
attgttgata gagcttatgc tgatgataat aatactttgt atttttataa ttggactgaa 120
tatgttcctc ctggattgtt ggaacaattt actaaggaaa ctggaattaa ggttatttat 180
tctacttatg aatctaatga aactatgtat gctaagttga agacttataa ggatggagct 240

-continued

```
tatgatttgg ttgttccttc tacttattat gttgataaga tgagaaagga aggaatgatt    300

caaaagattg ataagtctaa gttgactaat ttttctaatt tggatcctga tatgttgaat    360

aagccttttg atcctaataa tgattattct attccttata tttggggagc tactgctatt    420

ggagttaatg gagatgctgt tgatcctaag tctgttactt cttgggctga tttgtggaag    480

cctgaatata agggatcttt gttgttgact gatgatgcta gagaagtttt tcaaatggct    540

ttgagaaagt tgggatattc tggaaatact actgatccta aggaaattga agctgcttat    600

aatgaattga agaagttgat gcctaatgtt gctgctttta attctgataa tcctgctaat    660

ccttatatgg aaggagaagt taatttggga atgatttgga atggatctgc ttttgttgct    720

agacaagctg gaactcctat tgatgttgtt tggcctaagg aaggaggaat tttttggatg    780

gattctttgg ctattcctgc taatgctaag aataaggaag gagctttgaa gttgattaat    840

tttttgttga gacctgatgt tgctaagcaa gttgctgaaa ctattggata tcctactcct    900

aatttggctg ctagaaagtt gttgtctcct gaagttgcta atgataagac tttgtatcct    960

gatgctgaaa ctattaagaa tggagaatgg caaaatgatg ttggagctgc ttcttctatt   1020

tatgaagaat attatcaaaa gttgaaggct ggaagatag                          1059
```